US012773194B2

(12) United States Patent
Fahey et al.

(10) Patent No.: US 12,773,194 B2
(45) Date of Patent: Oct. 27, 2026

(54) IMPLANTABLE CLOSURE DEVICES AND ASSOCIATED SYSTEMS AND METHODS

(71) Applicant: Shifamed Holdings, LLC, Campbell, CA (US)

(72) Inventors: Brian Fahey, Menlo Park, CA (US); Ian Baranowski, Menlo Park, CA (US); David Rahdert, San Francisco, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 138 days.

(21) Appl. No.: 18/710,139

(22) PCT Filed: Dec. 19, 2022

(86) PCT No.: PCT/US2022/081907
§ 371 (c)(1),
(2) Date: May 14, 2024

(87) PCT Pub. No.: WO2023/122521
PCT Pub. Date: Jun. 29, 2023

(65) Prior Publication Data

US 2025/0090149 A1 Mar. 20, 2025

Related U.S. Application Data

(60) Provisional application No. 63/301,712, filed on Jan. 21, 2022, provisional application No. 63/291,652, filed on Dec. 20, 2021.

(51) Int. Cl.
*A61B 17/00* (2006.01)

(52) U.S. Cl.
CPC .... *A61B 17/00* (2013.01); *A61B 2017/00592* (2013.01); *A61B 2017/00597* (2013.01)

(58) Field of Classification Search
CPC .. A61B 2017/00592; A61B 2017/0097; A61B 2017/00606; A61B 2017/00243; A61B 2017/1139
See application file for complete search history.

(56) References Cited

U.S. PATENT DOCUMENTS

| | | | |
|---|---|---|---|
| 3,874,388 | A | 4/1975 | King et al. |
| 4,601,309 | A | 7/1986 | Chang |

(Continued)

FOREIGN PATENT DOCUMENTS

| | | |
|---|---|---|
| AU | 2005211243 | 8/2005 |
| AU | 2010344182 | 8/2012 |

(Continued)

OTHER PUBLICATIONS

International Search Report and Written Opinion received for International Application No. PCT/US2022/081907, filed Dec. 19, 2022; Applicant: Shifamed Holdings, LLC; Date of Mailing: May 23, 2023; 13 pages.

(Continued)

*Primary Examiner* — Alexander J Orkin
(74) *Attorney, Agent, or Firm* — Ashurst Perkins Coie US LLP

(57) ABSTRACT

The present technology is directed to implantable medical devices, systems, and methods for restricting, closing, or blocking an opening or defect in an anatomical structure. For example, many embodiments of the present technology are directed to implantable closure devices for plugging or sealing an opening in an anatomical structure separating a first body region and the second body region. In many of the embodiments described herein, the implantable closure devices are designed to be "recrossable," such that a catheter or other percutaneous tool can be passed through the closure device after the device has been implanted.

30 Claims, 7 Drawing Sheets

(56) References Cited

U.S. PATENT DOCUMENTS 4,662,355 A 5/1987 Pieronne et al.
4,705,507 A 11/1987 Boyles
4,836,204 A 6/1989 Landymore et al.
4,969,890 A 11/1990 Sugita et al.
4,979,955 A 12/1990 Smith
4,995,857 A 2/1991 Arnold
5,186,431 A 2/1993 Tamari
5,267,940 A 12/1993 Moulder
5,290,227 A 3/1994 Pasque
5,312,341 A 5/1994 Turi
5,326,374 A 7/1994 Ilbawi et al.
5,332,402 A 7/1994 Teitelbaum
5,334,217 A 8/1994 Das
5,409,019 A 4/1995 Wilk
5,429,144 A 7/1995 Wilk
5,500,015 A 3/1996 Deac
5,531,759 A 7/1996 Kensey et al.
5,556,386 A 9/1996 Todd
5,584,803 A 12/1996 Stevens et al.
5,597,377 A 1/1997 Aldea
5,645,559 A 7/1997 Hachtman et al.
5,655,548 A 8/1997 Nelson et al.
5,662,711 A 9/1997 Douglas
5,702,412 A 12/1997 Popov et al.
5,725,552 A 3/1998 Kotula et al.
5,741,297 A 4/1998 Simon
5,795,307 A 8/1998 Krueger
5,810,836 A 9/1998 Hussein et al.
5,824,071 A 10/1998 Nelson et al.
5,916,193 A 6/1999 Stevens et al.
5,941,850 A 8/1999 Shah et al.
5,957,949 A 9/1999 Leonhardt et al.
6,039,759 A 3/2000 Carpentier et al.
6,077,298 A 6/2000 Tu et al.
6,120,534 A 9/2000 Ruiz
6,126,686 A 10/2000 Badylak et al.
6,165,188 A 12/2000 Saadat et al.
6,210,318 B1 4/2001 Lederman
6,217,541 B1 4/2001 Yu
6,242,762 B1 6/2001 Brown et al.
6,254,564 B1 7/2001 Wilk et al.
6,260,552 B1 7/2001 Mortier et al.
6,270,526 B1 8/2001 Cox
6,277,078 B1 8/2001 Porat et al.
6,302,892 B1 10/2001 Wilk
6,328,699 B1 12/2001 Eigler et al.
6,344,022 B1 2/2002 Jarvik
6,358,277 B1 3/2002 Duran
6,406,422 B1 6/2002 Landesberg
6,447,539 B1 9/2002 Nelson et al.
6,451,051 B2 9/2002 Drasler et al.
6,458,153 B1 10/2002 Bailey et al.
6,468,303 B1 10/2002 Amplatz et al.
6,478,776 B1 11/2002 Rosenman et al.
6,491,705 B2 12/2002 Gifford, III et al.
6,494,889 B1 12/2002 Fleischman et al.
6,527,698 B1 3/2003 Kung et al.
6,544,208 B2 4/2003 Ethier et al.
6,562,066 B1 5/2003 Martin
6,572,652 B2 6/2003 Shaknovich
6,589,198 B1 7/2003 Soltanpour et al.
6,632,169 B2 10/2003 Korakianitis et al.
6,638,303 B1 10/2003 Campbell
6,641,610 B2 11/2003 Wolf et al.
6,652,578 B2 11/2003 Bailey et al.
6,685,664 B2 2/2004 Levin et al.
6,712,836 B1 3/2004 Berg et al.
6,911,043 B2 6/2005 Myers et al.
7,001,409 B2 2/2006 Amplatz
7,011,095 B2 3/2006 Wolf et al.
7,056,294 B2 6/2006 Khairkhahan et al.
7,149,587 B2 12/2006 Wardle et al.
7,175,656 B2 2/2007 Khairkhahan
7,270,675 B2 9/2007 Chun et al.
7,294,115 B1 11/2007 Wilk
7,311,690 B2 12/2007 Burnett
7,311,730 B2 12/2007 Gabbay
7,317,951 B2 1/2008 Schneider et al.
7,390,310 B2 6/2008 McCusker et al.
7,513,908 B2 4/2009 Lattouf
7,524,329 B2 4/2009 Rucker
7,524,330 B2 4/2009 Berreklouw
7,524,332 B2 4/2009 Osborne et al.
7,608,067 B2 10/2009 Bonni
7,665,466 B2 2/2010 Figulla et al.
7,699,059 B2 4/2010 Fonseca et al.
7,736,327 B2 6/2010 Wilk et al.
7,780,725 B2 8/2010 Haug et al.
7,794,473 B2 9/2010 Tessmer et al.
7,806,921 B2 10/2010 Hoffman
7,860,579 B2 12/2010 Goetzinger et al.
7,892,246 B2 2/2011 Akin et al.
7,905,901 B2 3/2011 Corcoran et al.
7,922,764 B2 4/2011 Gordy et al.
7,938,840 B2 5/2011 Golden et al.
7,967,769 B2 6/2011 Faul et al.
7,988,724 B2 8/2011 Salahieh et al.
8,012,198 B2 9/2011 Hill et al.
8,014,865 B2 9/2011 Najafi et al.
8,016,877 B2 9/2011 Seguin et al.
8,043,360 B2 10/2011 McNamara et al.
8,070,708 B2 12/2011 Rottenberg et al.
8,091,556 B2 1/2012 Keren et al.
8,096,959 B2 1/2012 Stewart et al.
8,147,545 B2 4/2012 Avior
8,157,860 B2 4/2012 McNamara et al.
8,172,896 B2 5/2012 McNamara et al.
8,235,916 B2 8/2012 Whiting et al.
8,235,933 B2 8/2012 Keren et al.
8,246,677 B2 8/2012 Ryan
8,252,042 B2 8/2012 McNamara et al.
8,255,062 B2 8/2012 Doan et al.
8,298,240 B2 10/2012 Giger et al.
8,303,511 B2 11/2012 Eigler et al.
8,348,996 B2 1/2013 Tuval et al.
8,398,708 B2 3/2013 Meiri et al.
8,460,366 B2 6/2013 Rowe
8,460,372 B2 6/2013 McNamara et al.
8,597,225 B2 12/2013 Kapadia
8,647,381 B2 2/2014 Essinger et al.
8,696,611 B2 4/2014 Nitzan et al.
8,696,693 B2 4/2014 Najafi et al.
8,740,962 B2 6/2014 Finch et al.
8,745,845 B2 6/2014 Finch et al.
8,747,458 B2 6/2014 Tuval et al.
8,752,258 B2 6/2014 Finch et al.
8,764,848 B2 7/2014 Callaghan et al.
8,827,888 B2 9/2014 Bolyard et al.
8,882,697 B2 11/2014 Celermajer et al.
8,932,247 B2 1/2015 Stergiopulos
8,951,223 B2 2/2015 McNamara et al.
D727,501 S 4/2015 Heipl
9,005,155 B2 4/2015 Sugimoto
9,034,034 B2 5/2015 Nitzan et al.
9,084,589 B2 7/2015 Moszner
9,138,213 B2 9/2015 Amin et al.
9,179,899 B2 11/2015 Freudenthal
9,205,236 B2 12/2015 McNamara et al.
9,232,997 B2 1/2016 Sugimoto et al.
9,277,995 B2 3/2016 Celermajer et al.
9,333,067 B2 5/2016 McKnight et al.
9,358,371 B2 6/2016 McNamara et al.
9,456,812 B2 10/2016 Finch et al.
9,629,715 B2 4/2017 Nitzan et al.
9,642,993 B2 5/2017 McNamara et al.
9,649,480 B2 5/2017 Sugimoto et al.
9,681,948 B2 6/2017 Levi et al.
9,707,382 B2 7/2017 Nitzan et al.
9,713,696 B2 7/2017 Yacoby et al.
9,724,499 B2 8/2017 Rottenberg et al.
9,737,264 B2 8/2017 Braido et al.
9,757,107 B2 9/2017 McNamara et al.
9,775,636 B2 10/2017 Fazio et al.
9,789,294 B2 10/2017 Taft et al.

(56) References Cited

U.S. PATENT DOCUMENTS 9,918,677 B2 3/2018 Eigler et al.
9,918,856 B2 3/2018 Favier et al.
9,937,036 B2 4/2018 Sugimoto et al.
9,943,670 B2 4/2018 Keren et al.
9,980,815 B2 5/2018 Nitzan et al.
10,045,766 B2 8/2018 McNamara et al.
10,076,403 B1 9/2018 Eigler et al.
10,098,551 B2 10/2018 Doan et al.
10,188,375 B2 1/2019 McNamara et al.
10,195,441 B2 2/2019 Kaiser et al.
10,207,087 B2 2/2019 Keren
10,251,740 B2 4/2019 Eigler et al.
10,292,690 B2 5/2019 Celermajer et al.
10,350,384 B2 7/2019 Farnan et al.
10,357,357 B2 7/2019 Levi et al.
10,368,981 B2 8/2019 Nitzan et al.
10,376,359 B2 8/2019 Essinger et al.
10,376,680 B2 8/2019 McNamara et al.
10,398,421 B2 9/2019 Celermajer
10,405,903 B1 9/2019 Biesinger et al.
10,413,284 B2 9/2019 McNamara et al.
10,413,286 B2 9/2019 McNamara et al.
10,463,477 B2 11/2019 Forcucci et al.
10,463,490 B2 11/2019 Rottenberg et al.
10,478,067 B2 11/2019 Najafi
10,478,594 B2 11/2019 Yacoby et al.
10,568,751 B2 2/2020 McNamara
10,588,611 B2 3/2020 Magnin et al.
10,595,999 B2 3/2020 Vettukattil et al.
10,610,210 B2 4/2020 Finch et al.
10,624,621 B2 4/2020 Celermajer
10,632,292 B2 4/2020 Forcucci et al.
10,639,459 B2 5/2020 Nitzan et al.
10,675,450 B2 6/2020 Finch
10,828,151 B2 11/2020 Nitzan et al.
10,835,394 B2 11/2020 Nae et al.
10,898,698 B1 1/2021 Eigler et al.
10,912,645 B2 2/2021 Rottenberg et al.
10,925,706 B2 2/2021 Eigler et al.
10,932,786 B2 3/2021 McNamara et al.
10,940,296 B2 3/2021 Keren
10,945,716 B2 3/2021 Chen et al.
11,135,410 B2 10/2021 Finch et al.
11,633,194 B2 4/2023 Alexander et al.
11,690,976 B2 7/2023 Yacoby et al.
11,813,386 B2 11/2023 Nae et al.
12,186,176 B2 1/2025 Eigler et al.
2002/0165606 A1 11/2002 Wolf et al.
2002/0169371 A1 11/2002 Gilderdale
2002/0169475 A1 11/2002 Gainor et al.
2002/0173742 A1 11/2002 Keren et al.
2002/0177891 A1 11/2002 Miles et al.
2003/0032967 A1 2/2003 Park et al.
2003/0120292 A1 6/2003 Park et al.
2003/0125798 A1 7/2003 Martin
2003/0127090 A1 7/2003 Gifford et al.
2003/0163190 A1 8/2003 LaFont et al.
2004/0016514 A1 1/2004 Nien
2004/0077988 A1 4/2004 Tweden et al.
2004/0088045 A1 5/2004 Cox
2004/0093075 A1 5/2004 Kuehne
2004/0147869 A1 7/2004 Wolf et al.
2004/0147939 A1 7/2004 Rabkin et al.
2004/0162514 A1 8/2004 Alferness et al.
2004/0210190 A1 10/2004 Kohler et al.
2004/0215067 A1 10/2004 Stiger et al.
2004/0215323 A1 10/2004 Stiger
2005/0033351 A1 2/2005 Newton
2005/0055082 A1 3/2005 Ben Muvhar et al.
2005/0143758 A1 6/2005 Abbott et al.
2005/0148925 A1 7/2005 Rottenberg et al.
2005/0165344 A1 7/2005 Dobak, III
2005/0192627 A1 9/2005 Whisenant et al.
2006/0025857 A1 2/2006 Bergheim et al.
2006/0111660 A1 5/2006 Wolf et al.
2007/0010837 A1 1/2007 Tanaka
2007/0010852 A1 1/2007 Blaeser et al.
2007/0043435 A1 2/2007 Seguin et al.
2007/0123917 A1 5/2007 Ortiz et al.
2007/0142907 A1 6/2007 Moaddeb et al.
2007/0213813 A1 9/2007 Von Segesser et al.
2008/0119891 A1 5/2008 Miles et al.
2008/0147111 A1 * 6/2008 Johnson ................ A61F 2/0103
606/200
2008/0215131 A1 9/2008 Magnuson et al.
2009/0243956 A1 10/2009 Keilman et al.
2009/0276040 A1 11/2009 Rowe et al.
2010/0057192 A1 3/2010 Celermajer
2010/0256753 A1 10/2010 McNamara et al.
2010/0298755 A1 11/2010 McNamara et al.
2011/0054515 A1 3/2011 Bridgeman et al.
2011/0218480 A1 9/2011 Rottenberg et al.
2011/0218481 A1 9/2011 Rottenberg et al.
2011/0257723 A1 10/2011 McNamara
2011/0295183 A1 12/2011 Finch et al.
2011/0306916 A1 * 12/2011 Nitzan ................ A61M 27/006
604/9
2012/0130301 A1 5/2012 McNamara et al.
2012/0172838 A1 7/2012 Flaherty et al.
2012/0265296 A1 10/2012 McNamara et al.
2012/0290062 A1 11/2012 McNamara et al.
2013/0165967 A1 6/2013 Amin et al.
2013/0197607 A1 8/2013 Wilder et al.
2014/0128796 A1 5/2014 Keren et al.
2014/0155768 A1 6/2014 Orion et al.
2014/0277054 A1 9/2014 McNamara et al.
2015/0034217 A1 2/2015 Vad
2015/0119796 A1 4/2015 Finch
2015/0148731 A1 5/2015 Mcnamara et al.
2015/0230843 A1 8/2015 Palmer et al.
2015/0320424 A1 11/2015 Gourlay
2016/0151179 A1 6/2016 Favier et al.
2016/0220357 A1 8/2016 Anand et al.
2016/0331382 A1 * 11/2016 Center ............. A61B 17/12122
2016/0374682 A1 12/2016 Leonard et al.
2017/0035435 A1 2/2017 Amin et al.
2017/0224323 A1 * 8/2017 Rowe ................. A61B 17/0218
2017/0273790 A1 9/2017 Vettukattil et al.
2017/0340460 A1 11/2017 Rosen et al.
2018/0014828 A1 1/2018 Fonte et al.
2018/0110468 A1 4/2018 Goldshtein et al.
2018/0243071 A1 8/2018 Eigler et al.
2018/0256865 A1 9/2018 Finch et al.
2018/0280667 A1 10/2018 Keren
2019/0021861 A1 1/2019 Finch
2019/0070421 A1 3/2019 Chen
2019/0254814 A1 8/2019 Nitzan et al.
2019/0262118 A1 8/2019 Eigler et al.
2019/0269392 A1 9/2019 Celermajer et al.
2019/0328513 A1 10/2019 Levi et al.
2019/0336163 A1 11/2019 McNamara et al.
2019/0374254 A1 12/2019 Arkvalos et al.
2020/0060825 A1 2/2020 Rottenberg et al.
2020/0078196 A1 3/2020 Rosen et al.
2020/0078558 A1 3/2020 Yacoby et al.
2020/0085600 A1 3/2020 Schwartz et al.
2020/0188143 A1 6/2020 McNamara
2020/0197178 A1 6/2020 Vecchio
2020/0229924 A1 7/2020 Chan et al.
2020/0229977 A1 7/2020 Mixter et al.
2020/0229982 A1 7/2020 Mixter et al.
2020/0245991 A1 8/2020 Celermajer
2020/0261705 A1 8/2020 Nitzan et al.
2020/0268515 A1 8/2020 Vettukattil et al.
2020/0306435 A1 10/2020 Vollmers et al.
2020/0315599 A1 10/2020 Nae et al.
2020/0368505 A1 11/2020 Nae et al.
2020/0391016 A1 12/2020 Passman et al.
2021/0052378 A1 2/2021 Nitzan et al.
2021/0059527 A1 3/2021 Najafi
2021/0085935 A1 3/2021 Fahey et al.
2021/0100665 A1 4/2021 Nae et al.
2021/0121179 A1 4/2021 Ben-david et al.
2021/0153776 A1 5/2021 Minar et al.

(56) References Cited

U.S. PATENT DOCUMENTS

| | | | |
|---|---|---|---|
| 2021/0177508 A1 | 6/2021 | Kellerman | |
| 2021/0259732 A1 | 8/2021 | Dicicco et al. | |
| 2021/0259829 A1 | 8/2021 | Quinn | |
| 2021/0259839 A1 | 8/2021 | Cole et al. | |
| 2021/0290214 A1 | 9/2021 | Cole et al. | |
| 2021/0299425 A1 | 9/2021 | Kume et al. | |
| 2021/0299430 A1 | 9/2021 | Ratz et al. | |
| 2021/0361257 A1 | 11/2021 | Eimer et al. | |
| 2021/0370032 A1 | 12/2021 | Fahey et al. | |
| 2022/0142652 A1 | 5/2022 | Alexander et al. | |
| 2022/0175364 A1 | 6/2022 | Rowe et al. | |
| 2022/0313426 A1 | 10/2022 | Gifford, III et al. | |
| 2022/0347446 A1 | 11/2022 | Fahey et al. | |
| 2023/0191093 A1 | 6/2023 | Nae et al. | |
| 2024/0399123 A1 | 12/2024 | Valdez et al. | |
| 2024/0416091 A1 | 12/2024 | Mahmoudi | |
| 2025/0090149 A1 | 3/2025 | Fahey et al. | |

FOREIGN PATENT DOCUMENTS

| | | |
|---|---|---|
| AU | 2011332324 | 6/2013 |
| AU | 2012214279 | 8/2013 |
| AU | 2018228451 | 9/2019 |
| CA | 2785041 | 8/2011 |
| CA | 24786575 | 8/2011 |
| CA | 2818417 | 5/2012 |
| CA | 2955389 | 1/2016 |
| CA | 3054891 | 9/2018 |
| CN | 101415452 | 4/2009 |
| CN | 102458316 | 5/2012 |
| CN | 102905626 | 1/2013 |
| CN | 103458832 | 12/2013 |
| CN | 105662653 | 6/2016 |
| CN | 109646063 | 4/2019 |
| CN | 109646063 A | 4/2019 |
| CN | 110536657 | 12/2019 |
| EP | 0326757 | 8/1989 |
| EP | 1658818 | 5/2006 |
| EP | 2097012 | 9/2009 |
| EP | 2528646 | 12/2012 |
| EP | 2642954 | 10/2013 |
| EP | 2967867 | 1/2016 |
| EP | 3087953 | 11/2016 |
| EP | 3291773 | 3/2018 |
| EP | 3329860 | 6/2018 |
| EP | 1771132 | 3/2019 |
| EP | 3579907 | 12/2019 |
| EP | 3589238 | 1/2020 |
| EP | 3624701 | 3/2020 |
| EP | 2999412 | 5/2020 |
| EP | 3705154 | 9/2020 |
| EP | 3716877 | 10/2020 |
| EP | 3740163 | 11/2020 |
| EP | 3766431 | 1/2021 |
| EP | 3834737 | 6/2021 |
| EP | 3843618 | 7/2021 |
| EP | 3871626 | 9/2021 |
| EP | 3886761 | 10/2021 |
| EP | 3893731 | 10/2021 |
| EP | 3897369 | 10/2021 |
| IL | 176973 | 12/2006 |
| IL | 221127 | 9/2012 |
| IL | 226374 | 7/2013 |
| IL | 215975 | 11/2016 |
| IL | 227756 | 6/2017 |
| IL | 220201 | 8/2017 |
| IL | 253648 | 9/2017 |
| IL | 255379 | 12/2017 |
| IL | 252395 | 4/2020 |
| IN | 2011KN04472 | 7/2012 |
| IN | 2012KN01275 | 2/2013 |
| IN | 2013KN01954 | 11/2013 |
| IN | 2013CN06525 | 8/2014 |
| IN | 2012KN01988 | 8/2016 |
| JP | 2007527742 | 10/2007 |
| JP | 2010508093 | 3/2010 |
| JP | 2013046784 | 3/2013 |
| JP | 2014503246 | 2/2014 |
| JP | 2014512869 | 5/2014 |
| JP | 2020509812 | 4/2020 |
| WO | WO2001030230 | 5/2001 |
| WO | WO2001072367 | 10/2001 |
| WO | WO2001095783 | 12/2001 |
| WO | WO2005074367 | 8/2005 |
| WO | WO2006089236 | 8/2006 |
| WO | WO2007083288 | 7/2007 |
| WO | WO2008055301 | 5/2008 |
| WO | WO2010128501 | 11/2010 |
| WO | WO2010129089 | 11/2010 |
| WO | WO2011093941 | 8/2011 |
| WO | WO2011094521 | 8/2011 |
| WO | WO2012071075 | 5/2012 |
| WO | WO2012085913 | 6/2012 |
| WO | WO2012109557 | 8/2012 |
| WO | WO2013014539 | 1/2013 |
| WO | WO2013096965 | 6/2013 |
| WO | WO2014150106 | 9/2014 |
| WO | WO2014188279 | 11/2014 |
| WO | WO2016014821 | 1/2016 |
| WO | WO2016038115 | 3/2016 |
| WO | WO2016178171 | 11/2016 |
| WO | WO2017151566 | 9/2017 |
| WO | WO2018158747 | 9/2018 |
| WO | WO2019018807 | 1/2019 |
| WO | WO2019142152 | 7/2019 |
| WO | WO2019179447 | 9/2019 |
| WO | WO2019188917 | 10/2019 |
| WO | WO2019189079 | 10/2019 |
| WO | WO2019209420 | 10/2019 |
| WO | WO2020094085 | 5/2020 |
| WO | WO2020094087 | 5/2020 |
| WO | WO2020094094 | 5/2020 |
| WO | WO2020110048 | 6/2020 |
| WO | WO2020123338 | 6/2020 |
| WO | WO2020202046 | 10/2020 |
| WO | WO2020206062 | 10/2020 |
| WO | WO2020215090 | 10/2020 |
| WO | WO2020217194 | 10/2020 |
| WO | WO2020219265 | 10/2020 |
| WO | WO2020225698 | 11/2020 |
| WO | WO2020225757 | 11/2020 |
| WO | WO2020229636 | 11/2020 |
| WO | WO2020234751 | 11/2020 |
| WO | WO2020251700 | 12/2020 |
| WO | WO2020257530 | 12/2020 |
| WO | WO2020259492 | 12/2020 |
| WO | WO2021025905 | 2/2021 |
| WO | WO2021026485 | 2/2021 |
| WO | WO2021034573 | 2/2021 |
| WO | WO2021046753 | 3/2021 |
| WO | WO2021055264 | 3/2021 |
| WO | WO2021065873 | 4/2021 |
| WO | WO2021065874 | 4/2021 |
| WO | WO2021065875 | 4/2021 |
| WO | WO2021065912 | 4/2021 |
| WO | WO2021086707 | 5/2021 |
| WO | WO2021091566 | 5/2021 |
| WO | WO2021096766 | 5/2021 |
| WO | WO2021101707 | 5/2021 |
| WO | WO2021113670 | 6/2021 |
| WO | WO2021136252 | 7/2021 |
| WO | WO2021136261 | 7/2021 |
| WO | WO2021138041 | 7/2021 |
| WO | WO2021146342 | 7/2021 |
| WO | WO2021150761 | 7/2021 |
| WO | WO2021158559 | 8/2021 |
| WO | WO2021162888 | 8/2021 |
| WO | WO2021178636 | 9/2021 |
| WO | WO2021190547 | 9/2021 |
| WO | WO2021212011 | 10/2021 |
| WO | WO2021224736 | 11/2021 |
| WO | WO2022091018 | 5/2022 |
| WO | WO2022192382 | 9/2022 |

(56) References Cited

FOREIGN PATENT DOCUMENTS

| | | |
|---|---|---|
| WO | WO2023122521 | 6/2023 |
| WO | WO2024137816 | 6/2024 |
| WO | WO2024249425 | 12/2024 |

OTHER PUBLICATIONS

Jodi Perkins, "Corvia Medical and physIQ Partner in Global Phase 3 Heart Failure Clinical Trial to Leverage Novel Digital Endpoints," Press Release, 2019 Copyright, Medical Alley Association, 3 pages.
Lehner et al., "The Creation of an Interatrial Right-To-Left Shunt in Patients with Severe, Irreversible Pulmonary Hypertension: Rationale, Devices, Outcomes," Current Cardiology Reports (2019) 21: 31, https://doi.org/10.1007/s11886-019-1118-8; 9 pages.
Ando et al., "Left ventricular decompression through a patent foramen ovale in a patient with hypertrophic cardiomyopathy: a case report," Cardiovascular Ultrasound vol. Article No. 2 (2004).
Braunwald, Heart Disease, Chapter 6, 2015, p. 186.
Bridges et al., "The Society of Thoracic Surgeons practice guideline series: transmyocardial laser revascularization," The Annals of Thoracic Surgery, vol. 77, Issue 4, Apr. 2004, pp. 1494-1502.
Bristow et al., "Improvement in cardiac myocyte function by biological effects of medical therapy: A new concept in the treatment of heart failure," European Heart Journal, vol. 16, Issue suppl. F, Jul. 1995, pp. 20-31.
Case et al., "Relief of High Left-Atrial Pressure in Left-Ventricular Failure," Lancet, Oct. 17, 1964, pp. 841-842.
Coats et al., "Controlled trial of physical training in chronic heart failure. Exercise performance, hemodynamics, ventilation, and autonomic function," Circulation, 1992;85:2119-2131.
Davies et al., "Reduced contraction and altered frequency response of isolated ventricular myocytes from patients with heart failure," Circulation, (1995), 92:2540-2549, Circulation, (1995), 92:2540-2549.
Ennezat et al., "An unusual case of low-flow, low gradient severe aortic stenosis: Left-to-right shunt due to atrial septal defect," Cardiology, (2009), 113(2):146-148.
Ewert et al., "Masked Left Ventricular Restriction in Elderly Patients With Atrial Septal Defects: A Contraindication for Closure," Catheterization and Cardiovascular Interventions, 52: 177-180, 2001.
Ewert et al., "Acute left heart failure after interventional occlusion of an atrial septal defect," Z. Kardiol.,Catheterization and Cardiovascular Interventions, (May 2001), 90(5):362-366.
Geiran et al., "Changes in cardiac dynamics by opening an interventricular shunt in dogs," J. Surg. Res., (Jan. 1990), 48(1):6-12.
Gelernter-Yaniv et al., "Transcatheter closure of left-to-right interatrial shunts to resolve hypoxemia," Congenit. Heart Dis., (Jan. 2008), 31(1):47-53.
Gewillig et al., "Creation with a stent of an unrestrictive lasting atrial communication," Cardio. Young, (2002), 12(4):404-407.
Khositseth et al., "Transcatheter Amplatzer Device Closure of Atrial Septal Defect and Patent Foramen Ovale in Patients With Presumed Paradoxical Embolism," Mayo Clinic Proc., 79:35-41 (2004).
Kramer et al., "Controlled study of captopril in chronic heart failure: A rest and exercise hemodynamic study," Circulation, (1983), 67(4):807-816.
Lai et al., "Bidirectional shunt through a residual atrial septal defect after percutaneous transvenous mitral commissurotomy," Cardiology, (1993), 83(3):205-207.
Lemmer et al., "Surgical implications of atrial septal defect complicating aortic balloon valvuloplasty," Ann. thorac. Surg., (Aug. 1989), 48(2):295-297.
Park et al., "Blade atrial septostomy: collaborative study," Circulation, 66(2):258-266 (1982).
Roven et al., "Effect of Compromising Right Ventricular Function in Left Ventricular Failure by Means of Interatrial and Other Shunts," American Journal Cardiology, 24:209-219 (1969).
Salehian et al., "Improvements in Cardiac Form and Function After Transcatheter Closure of Secundum Atrial Septal Defects," Journal of the American College of Cardiology, 45(4):499-504 (2005).
Schmitto et al., "Chronic heart failure induced by multiple sequential coronary microembolization in sheep," The International Journal of Artificial Organs, 31(4):348-353 (2008).
Schubert et al., "Left ventricular conditioning in the elderly patient to prevent congestive heart failure after transcatheter closure of the atrial septal defect," Catheter Cardiovasc. Interv., (2005), 64(3):333-337.
Stormer et al., "Comparative study of in vitro flow characteristics between a human aortic valve and a designed aortic and six corresponding types of prosthetic heart valves," European Surgical Research, (1976), 8(2):117-131.
Stumper et al., "Modified technique of stent fenestration of the atrial septum, Heart," (2003), 89:1227-1230.
Trainor et al., "Comparative Pathology of an Implantable Left Atrial Pressure Sensor," ASAIO Journal, Clinical Cardiovascular/Cardiopulmonary Bypass, 59(5):486-92 (2013).
Zhou et al., "Unidirectional valve patch for repair of cardiac septal defects with pulmonary hypertension," Annals of Thoracic Surgeons, 60: 1245-1249, 1995.

* cited by examiner

IMPLANTABLE CLOSURE DEVICES AND ASSOCIATED SYSTEMS AND METHODS

CROSS-REFERENCE TO RELATED APPLICATION(S)

This application is a 35 U.S.C. § 371 U.S. National Phase application of International Patent Application No. PCT/US2022/081907, filed Dec. 19, 2022, and titled IMPLANTABLE CLOSURE DEVICES AND ASSOCIATED SYSTEMS AND METHODS, which claims the benefit of U.S. Provisional Patent Application No. 63/291,652, filed Dec. 20, 2021, and U.S. Provisional Patent Application No. 63/301,712, filed Jan. 21, 2022, each of which is incorporated by reference herein in its entirety.

TECHNICAL FIELD

The present technology generally relates to implantable medical devices and, in particular, to implantable closure devices for closing openings in anatomical structures.

BACKGROUND

Various anatomical disorders are characterized by a defect in an anatomical structure that fluidly connects a first body region and a second body region that generally would not be connected absent the defect. For example, patients having a patent foramen ovale (PFO) or an atrial septal defect (ASD) have an opening in the septal wall of their heart between the left atrium and the right atrium. Depending on the size and severity of the PFO or ASD, it can be treated by implanting a closure device that permanently occludes the opening.

Various medical procedures also create punctures or openings in anatomical structures that separate a first body region and a second body region. For example, numerous heart-related medical procedures are performed using a transvascular approach in which a catheter is inserted into a patient's blood vessel (e.g., a femoral vein) and advanced toward the patient's heart through their vasculature. Depending on the location of the procedure in the heart, the catheter may need to pass through the atrial septum. For example, for procedures that take place in the left atrium, a catheter generally must puncture the atrial septum before the procedure is performed. Examples of procedures performed using a trans-septal puncture include atrial fibrillation therapy, left atrial appendage closure, percutaneous mitral valve repair, and percutaneous mitral valve replacement. Following the procedure, the catheter is withdrawn from the patient's vasculature. However, the puncture or opening in the atrial septum remains. During certain procedures that require these punctures or openings to be large, they are generally sealed using a plug or other static closure device that permanently occludes the septal opening.

DETAILED DESCRIPTION

Figure 1A:
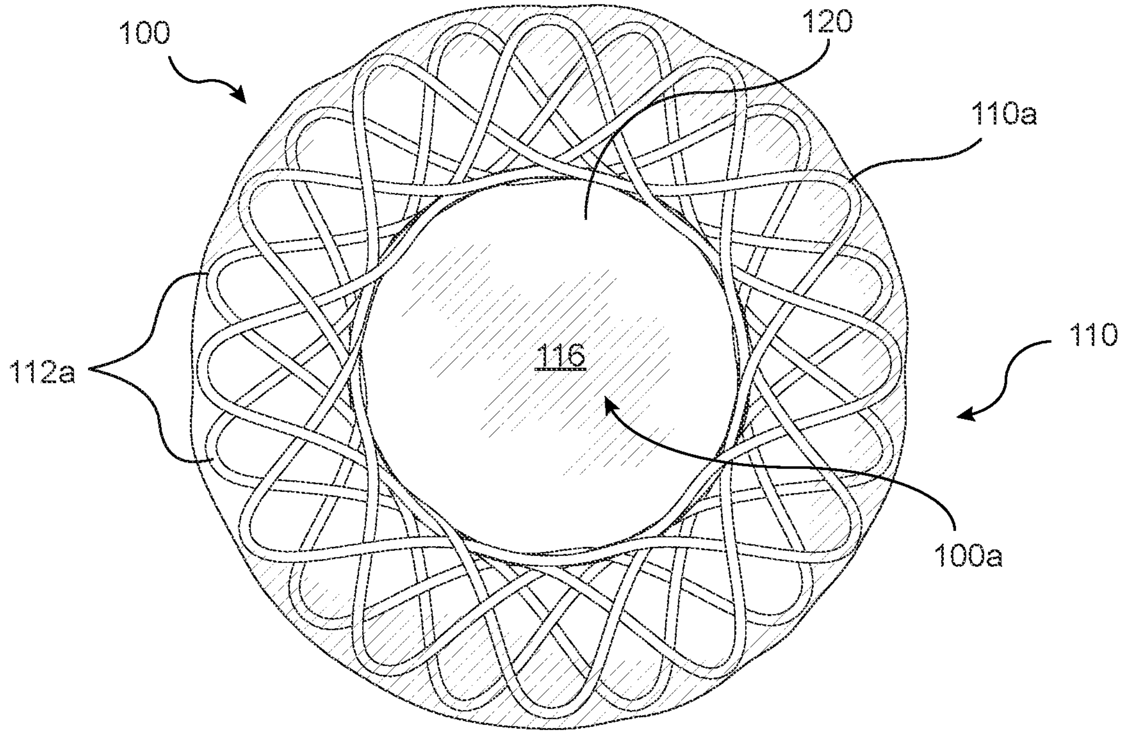
FIGS. 1A-1C illustrate an implantable closure device configured in accordance with select embodiments of the present technology.

The present technology is directed to implantable medical devices, systems, and methods for restricting, closing, or blocking an opening or defect in an anatomical structure. For example, many embodiments of the present technology are directed to implantable closure devices for plugging or sealing an opening in an anatomical structure separating a first body region and a second body region. In many of the embodiments described herein, the implantable closure devices are designed to be "recrossable," such that a catheter or other percutaneous tool can be passed through the closure device after the device has been implanted.

The implantable closure devices describe herein generally include an anchor structure that passes through or is positioned proximate to the opening and secures the device to the anatomical structure. The implantable closure device can also include a membrane affixed to or otherwise covering a portion of the anchor structure to block flow through the opening. In some embodiments, the implantable closure device further includes one or more structural members embedded within or otherwise coupled to the membrane. As described in detail throughout the following Detailed Description, the structural members can (1) reduce or prevent tearing of the membrane or patient tissue during a subsequent recrossing of the closure device, and (2) can facilitate quick reclosure of the device following a recrossing of the closure device.

Closure devices described in the prior art are challenging to recross once deployed, essentially creating a permanent barrier and therefore reduced or even eliminated access to the anatomical region on the distal side of the device. To the extent recrossing is even possible, it is time consuming and arduous, and results in a permanently damaged device that leaves behind a hole that can be detrimental to a patient's health. In contrast, the closure devices described herein are expected to more easily allow for closure of various anatomical openings or defects (e.g., between a first body region and a second body region) and subsequent recrossing of the device (e.g., from the first body region into the second body region). For example, the closure devices described herein enable closure of atrial-septal defects (ASDs) and/or residual openings created by septal punctures associated with the large-bore catheter crossings required for certain transseptal procedures. In embodiments in which the closure device is implanted across the septal wall, the recrossability of the closure device may enable additional transseptal procedures to be performed, even after the closure device has been implanted. In fact, in many of the embodiments described herein, the closure devices can be recrossed any number of times without the need to remove the closure device prior to crossing, and without the need to actively "reclose" the closure device after recrossing. For example, the closure device can be configured such that, following a recrossing, the closure device automatically returns to a state in which the opening or puncture is relatively small (e.g., having a dimension less than 5 mm, less than 3 mm etc.), and thus expected to be overgrown by tissue within a relatively short time (e.g., less than one week, less than one month, less than three months, etc.). Accordingly, as described in greater detail below, the present technology provides improved closure devices that are recrossable.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1A-6.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

As used herein, the use of relative terminology, such as "about", "approximately", "substantially" and the like refer to the stated value plus or minus ten percent. For example, the use of the term "about 100" refers to a range of from 90 to 110, inclusive. In instances in which the context requires otherwise and/or relative terminology is used in reference to something that does not include a numerical value, the terms are given their ordinary meaning to one skilled in the art.

Figure 1B:
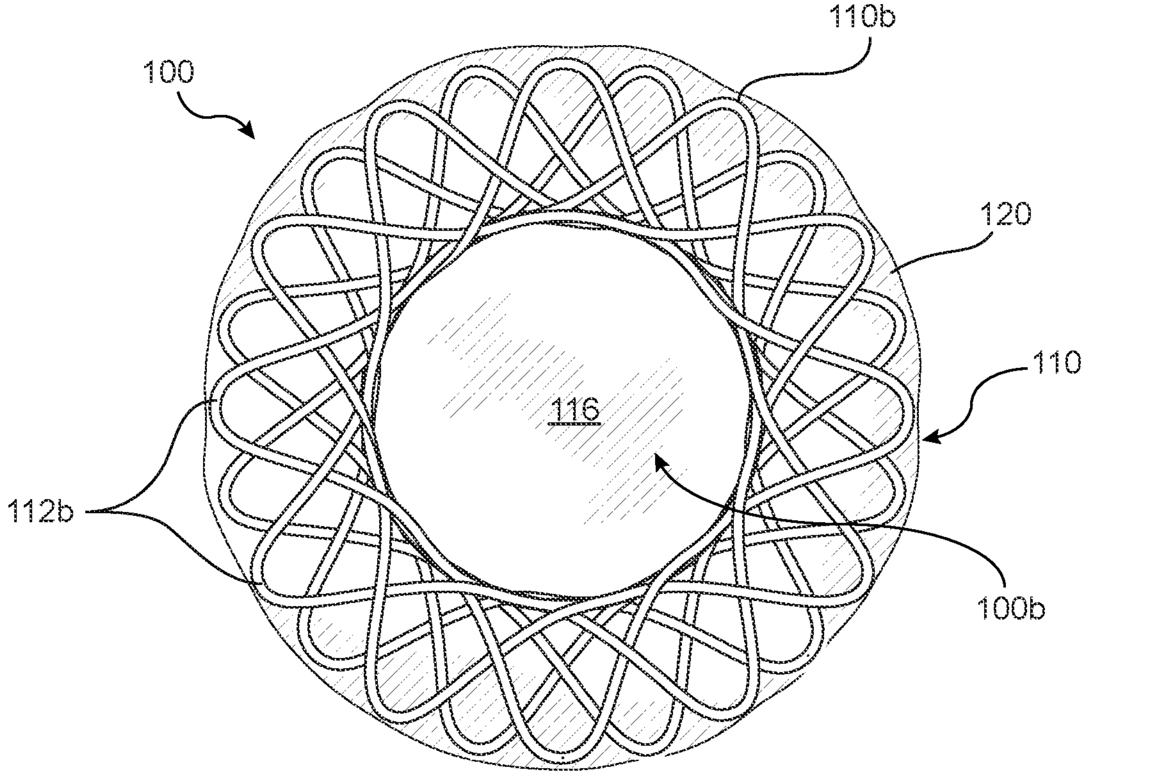
Figure 1C:
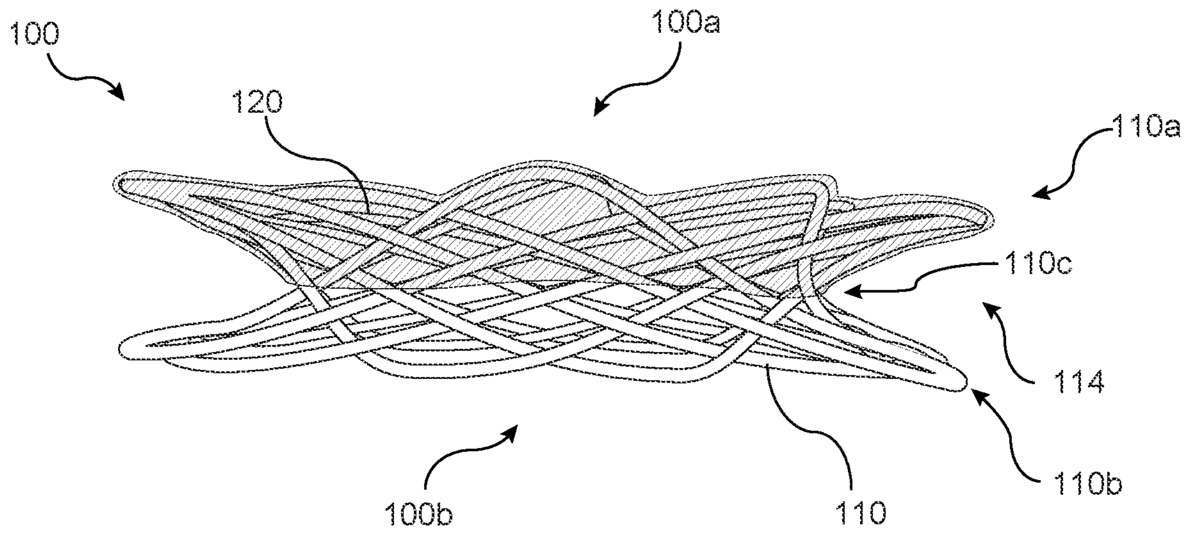

FIGS. 1A-1C illustrate a closure device 100 ("the device 100") in a deployed configuration and configured in accordance with select embodiments of the present technology. More specifically, FIG. 1A is a view of a first side 100*a* of the device 100, FIG. 1B is a rear view of a second side 100*b* of the device 100, and FIG. 1C is a side view of the device 100 showing both the first side 100*a* and the second side 100*b*. As described in detail below, the device 100 can be configured to partially or fully cover or occlude an opening or other defect in an anatomical structure, such as an ASD, PFO, or transeptal puncture in a septal wall. In operation, the device 100 can therefore reduce or prevent undesired fluid flow through the opening or defect in the anatomical structure.

Referring first to FIGS. 1A and 1B, the device 100 generally includes a frame or anchor structure 110. The anchor structure 110 can include a first anchoring portion 110*a* on the first side 100*a* of the device 100 (FIG. 1A), a second anchoring portion 110*b* on the second side 100*b* of the device 100 (FIG. 1B) opposite the first side 100*a*, and a neck portion 110*c* (FIG. 1C) extending between and coupling the first anchoring portion 110*a* and the second anchoring portion 110*b*. In the illustrated embodiment, the anchor structure 110 has an at least partial toroid shape such that there is an aperture or empty space 116 extending through a central portion of the anchor structure 110. As best shown in FIG. 1C, the first anchoring portion 110*a* and the second anchoring portion 110*b* generally have an outer circumference or other dimension that is greater than an outer circumference or dimension of the neck portion 110*c*. Accordingly, there is a gap 114 between the first anchoring portion 110*a* and the second anchoring portion 110*b* such that the anchor structure 110 has an H-shape when viewed from the side. In other embodiments, the anchor structure 110 can have other suitable shapes when viewed from the side, such as an X-shape or a diamond shape. As described in detail below, the device 100 can be configured to receive tissue within the gap 114 to secure the device 100 to patient tissue.

In some embodiments, the anchor structure 110 can be a single unitary component. For example, the anchor structure 110 can be a single wire or filament (e.g., a braided or woven wire structure) that forms the first anchoring portion 110*a*, the second anchoring portion 110*b*, and the neck portion 110*c*. As another example, the anchor structure 110 can be laser cut from a sheet, tube, or other piece of material. In other embodiments, the anchor structure 110 can be composed of multiple individual components. For example, the first anchoring portion 110*a* can be formed by a first wire or filament, the second anchoring portion 110*b* can be formed by a second wire or filament, and the neck portion 110*c* can be formed by a third wire or filament. As another example, the first anchoring portion 110*a* can be laser cut from a first piece of material, the second anchoring portion 110*b* can be laser cut from a second piece of material, and the neck portion 110*c* can be laser cut from a third piece of material. The foregoing components can then be welded, soldered, crimped, glued, or otherwise linked together to form the anchor structure 110. In embodiments in which the anchor structure 110 is composed of multiple components, individual components of the multiple components can be coupled or joined before implantation or during the implant procedure (e.g., at the target implantation site). Of course, the present technology is not limited to the specific compositions described herein, and the anchor structure 110 can be formed using other suitable materials and/or techniques.

The first anchoring portion 110*a* and the second anchoring portion 110*b* can be at least partially biased toward one another such that the first anchoring portion 110*a* and the second anchoring portion 110*b* at least partially squeeze patient tissue received within the gap 114 to secure the device 100 to patient tissue. For example, referring to FIGS. 1A and 1B, an outer circumferential portion 112*a* of the first anchoring portion 110*a* and a corresponding outer circumferential portion 112*b* of the second anchoring portion 110*b* can be biased toward one another. Accordingly, in embodiments in which the device 100 is deployed across an anatomical structure dividing a first body region and a second body region, the first anchoring portion 110*a* may reside within the first body region, the second anchoring portion 110*b* may reside within the second body region, the neck portion 110*c* may occupy/traverse an opening in the anatomical structure, and the gap 114 may receive a portion of the anatomical structure. The biasing force between the outer circumferential portion 112*a* of the first anchoring portion 110*a* and the outer circumferential portion 112*b* of the second anchoring portion 110*b* can form a slight clamping force on the portion of the anatomical structure positioned within the gap 114.

The anchor structure 110 can be at least partially composed of a self-expanding material or otherwise be configured to be self-expanding such that, after being exposed to stress and strain induced by being collapsed into a delivery tool (e.g., catheter, sheath, etc.) for delivery, it exhibits a response (e.g., an elastic response) to being deployed at body temperature. For example, the anchor structure 110 can be composed of nitinol that has an austenite finish temperature below body temperature. Accordingly, the anchor structure 110 can automatically deploy (e.g., self-expand without additional input or manipulation by a clinician) from a collapsed delivery configuration (e.g., as positioned in a delivery tool such as a catheter or sheath; not shown) to an expanded deployed configuration (shown in FIGS. 1A-1C) when released from the delivery tool. In some embodiments, the self-expanding or superelastic properties of the anchor structure 110 may also enable the anchor structure 110 to resist plastic mechanical deformation once deployed, and thus can provide a generally stable anchoring mechanism for the device 100. In other embodiments, the anchor structure 110 can be composed of a material that is not self-expanding at body temperature. In one example, the anchor structure 110 can be composed of nitinol that has an austenite finish temperature above body temperature. In such an example, the anchor structure 110 can be initially released from a delivery tool in a preliminary position (e.g., the collapsed delivery configuration, an intermediate configuration, etc.) and subsequently be heated above the austenite finish temperature to transition the shape of the anchor structure 110 toward the deployed configuration. In a second example, the anchor structure 110 can be composed of a material such as stainless steel (e.g., 316L), titanium alloy (e.g., $TiAl_6V_4$), cobalt chromium alloy (e.g., L605), or polymer (e.g., PEEK).

In some embodiments, the neck portion 110*c* of the anchor structure 110 is designed, manufactured, and/or selected to have an outer circumference or other dimension that is greater than the size of the hole or opening in the anatomical structure in which it is deployed. In such embodiments, when the device 100 is deployed at an opening, the neck portion 110*c* expands radially outward within the opening and contacts tissue. In some embodiments, this reshapes the opening. For example, deploying the device 100 in an opening can cause the opening to assume a shape that matches the outer perimeter of the neck portion 110*c*. In the illustrated embodiment, the outer perimeter of the neck portion 110*c* is generally circular (FIG. 1C), so the device 100 would reshape the opening to have a circular shape. However, other suitable shapes are possible by varying the shape of the outer circumference of the neck portion 110*c*. In some embodiments, the neck portion 110*c* has a length about the same as or greater than the thickness of the tissue at the anatomical structure (e.g., the thickness of the septal wall) such that forces applied by the device 100 to the anatomical structure are distributed across a volume of the anatomical structure.

In some embodiments, deploying the device 100 in the opening may also increase the size of the opening if the outer perimeter of the neck portion 110*c* is greater than the size of the opening. For example, the neck portion 110*c* may expand and/or re-shape a native defect in the anatomical structure, a slit made in the anatomical structure for a catheter crossing, etc. However, this is expected to be beneficial for several reasons. For example, attempting to "close" the opening or defect by stretching and connecting tissue can induce tearing in the tissue, both adjacent and spaced apart from the opening. Moreover, by expanding the size of the opening with the device 100, the rigid components of the device 100 (e.g., the anchor structure 110) are pushed radially outward, leaving a central region of the device free from rigid structures. As described in detail below, this is beneficial because it enables the device 100 to be "recrossed," enabling future catheter-based procedures.

Referring collectively to FIGS. 1A-1C, the device 100 can further include a membrane 120 coupled to the anchor structure 110 (portions of the membrane 120 are shown in FIGS. 1A-1C with surface shading lines for ease of illustration). For example, the membrane 120 can be directly attached to the anchor structure 110 (e.g., via suturing, welding, crimping, gluing, molding, stapling, curing/bonding, etc.), integrated with the anchor structure 110 (e.g., to form a unitary component), encapsulate the anchor structure 110 (e.g., via lamination), etc. As shown in FIG. 1A, the membrane 120 can extend at least partially or fully across the aperture 116 extending through the anchor structure 110. However, the membrane 120 can also extend outward beyond the aperture 116, e.g., to an outer circumference of the anchor structure. 110. In the illustrated embodiment, the membrane 120 is shown only on the first side 100*a* of the device 100. However, in other embodiments the membrane 120 can be on the second side 100*b* in addition to or in lieu of being on the first side 100*a*. In some embodiments, the neck portion 110*c* of the anchor structure 110 also includes a membrane 120 or other material that fills the portion of the aperture 116 extending therethrough.

The membrane 120 can be composed of a semi-flexible and at least partially impermeable material to prevent or at least reduce the flow of fluid through the aperture 116 in the anchor structure 110. For example, the membrane 120 can be composed of silicone, polytetrafluoroethylene (PTFE), expanded polytetrafluoroethylene (ePTFE), polyethylene terephthalate (PET), a urethane, nylon, or other similar material. In some embodiments, the membrane 120 can be composed of a composite material. In such embodiments, the composite material can be a hybrid material blend (e.g., mixed chemistry material, two fabrics woven or braided together, etc.) or be two or more sheets of different materials that are functionally integrated (e.g., a silicone membrane sandwiched between two ePTFE sheets). These hybrid materials may be useful to allow for the membrane 120 to simultaneously exhibit numerous desirable material properties. For example, an ePTFE/silicone composite membrane may aid in the promotion of rapid endothelialization and tissue overgrowth while retaining some of the inherent elasticity of a silicone material.

In some embodiments, the membrane 120 can be composed of a material or a blend of materials that mimic one or more structural properties of the tissue proximate the opening or defect in the anatomical structure the device 100 is configured to be deployed across. In such embodiments, the membrane 120 can provide similar resistance to puncture as the native tissue. As described in detail below, this is expected to be useful during a recrossing event in which a physician advances a percutaneous puncture tool through the membrane 120. In some embodiments, the membrane 120 may have a rough or textured surface (e.g., as opposed to a smooth surface). In some embodiments, the membrane may have a type A durometer of between about 65A and about 95A, or between about 70A and about 95A, or between about 75A and about 90A, or between about 80A and about 90A. The membrane 120 may also be configured so that it can be visualized using fluoroscopy, echocardiography, or another suitable technique. For example, the membrane 120 may be configured such that it tents to a degree that can be visualized using echocardiography but not so much that the membrane 120 may spontaneously tear or otherwise rupture.

In operation, the device 100 can be deployed at an opening or other defect in an anatomical structure dividing a first body region and a second body region. For example, following a procedure in which the septal wall between a left atrium and a right atrium was punctured to provide access to the left atrium to perform a medical procedure, the device 100 can be deployed in the puncture hole in the septal wall.

As previously described, when the device 100 is deployed from a catheter, it automatically self-expands into the deployed configuration shown in FIGS. 1A-1C and is anchored across the septal wall. Depending on the size of the puncture, the expansion of the device may (1) reshape the opening (as described previously) to correspond to the shape of the outer perimeter of the portion of the device 100 extending through the puncture, (2) expand the cross-sectional area of the opening, and (3) partially or fully fluidically seal the opening to reduce or prevent undesired fluid flow through the septal wall, e.g., between the left atrium and the right atrium (or vice versa). Moreover, as described in detail below, the device 100 can also enable access to the left atrium to facilitate future medical procedures that require a catheter-based approached through the septal wall. For example, if the patient requires an additional left atrial procedure after the device 100 has been implanted (e.g., days, months, or even years after implantation), a catheter with a puncturing element, angled dilator, balloon dilator, or other percutaneous tool can be advanced through the patient's vasculature and used to puncture the membrane 120 covering the aperture 116 through the anchor structure 110 (e.g., after identifying the aperture 116 using fluoroscopy, echocardiography, or another suitable technique). Because the rigid components of the device 100 are positioned radially outward, a catheter or other percutaneous tool can be advanced through the aperture 116 and into the left atrium to enable a procedure to be performed. Such procedure is referred to herein as a "recrossing," since it involves advancing a catheter through the previously implanted closure device 100. In some embodiments, the membrane 120 can be configured to provide tactile feedback (e.g., resistance) to the physician during the recrossing event that is similar to tactile feedback that would be experienced if the physician were puncturing native patient tissue (e.g., native septal wall tissue). As described below, the device 100 may optionally have one or more features that help reduce or prevent tissue tearing during the recrossing and/or help promote resealing of the membrane 120 following recrossing to once again fluidly isolate the left atrium and the right atrium.

Figure 1D:
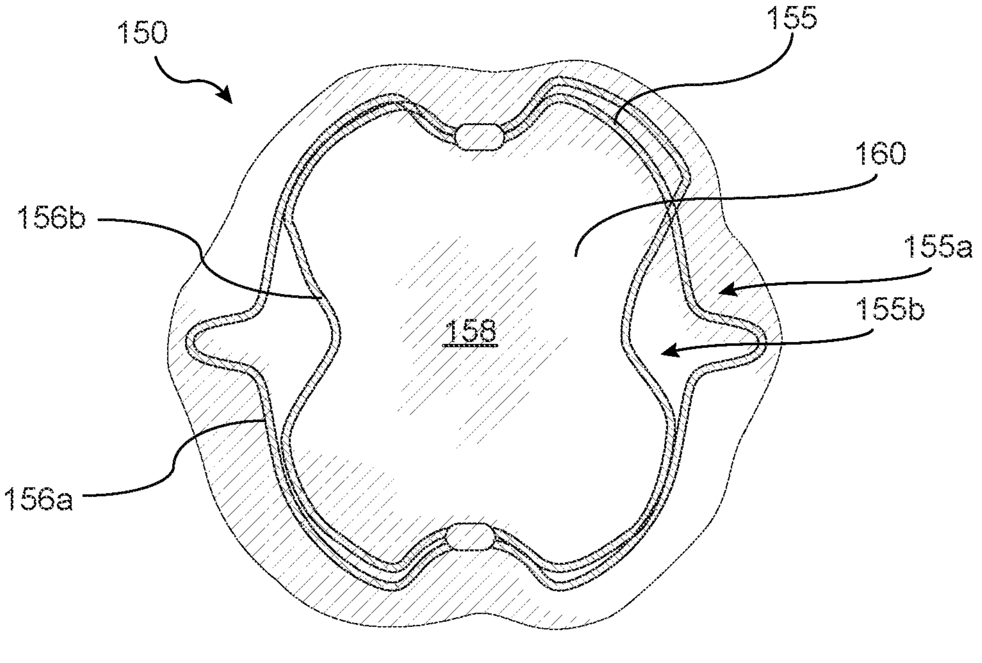
FIGS. 1D and 1E illustrate additional implantable closure devices configured in accordance with select embodiments of the present technology.
Figure 1E:
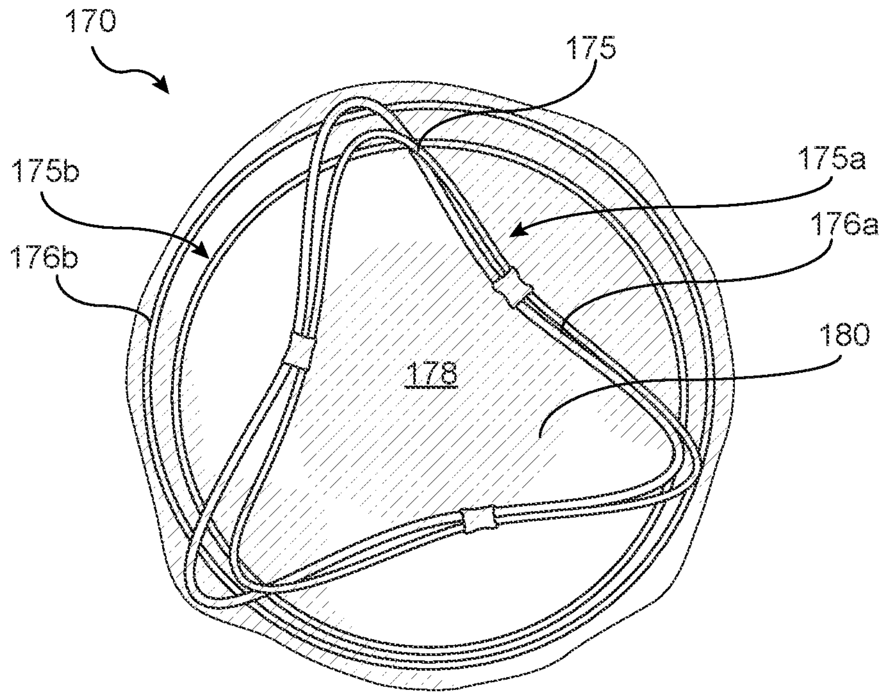

The closure devices in general, and the anchor structures in particular, can have other configurations beyond those shown in FIGS. 1A-1C. For example, FIGS. 1D and 1E illustrate additional closure devices configured in accordance with embodiments of the present technology. In particular, FIG. 1D illustrates a closure device 150 having an anchor structure 155, an aperture or empty space 158 extending through a central portion of the anchor structure 155, and a membrane 160 coupled to the anchor structure 155 and extending over the aperture 158 (portions of the membrane 160 are shown with surface shading lines for ease of illustration). The anchor structure 155 and the membrane 160 can be generally similar to the anchor structure 110 and the membrane 120 of the device 100. For example, the anchor structure 155 can have a first anchoring portion **155*a* configured to reside on a first side of an anatomical structure across which the device 150 is deployed, and a second anchoring portion 155*b* configured to reside on a second side of the anatomical structure. The first anchoring portion 155*a* and the second anchoring portion 155*b* can be separated by a neck portion (not shown), which can be the same as or generally similar to the neck portion 110*c* of the device 100 (FIG. 1C). However, the anchor structure 155 has a different shape than the anchor structure 110. For example, the first anchoring portion 155*a* includes one or more first loops 156*a*, and the second anchoring portion 155*b* includes one or more second loops 156*b*. In some embodiments in which there are multiple first loops 156*a* or multiple second loops 156*b*, the multiple first loops 156*a* can be arranged in a stacked configuration in which the multiple first loops 156*a* substantially overlap, and/or the multiple second loops 156*b* can be arranged in a stacked configuration in which the multiple second loops 156*b* substantially overlap. In some embodiments, the one or more first loops 156*a* and the one or more second loops 156*b*** have substantially the same shape.

FIG. 1E illustrates a closure device 170 having an anchor structure 175, an aperture or empty space 178 extending through a central portion of the anchor structure 175, and a membrane 180 coupled to the anchor structure and extending over the aperture 178 (portions of the membrane 180 are shown with surface shading lines for ease of illustration). The anchor structure 175 and the membrane 180 can be generally similar to the anchor structure 110 and the membrane 120 of the device 100. For example, the anchor structure 175 can have a first anchoring portion **175*a* configured to reside on a first side of an anatomical structure across which the device 170 is deployed, and a second anchoring portion 175*b* configured to reside on a second side of the anatomical structure. The first anchoring portion 175*a* and the second anchoring portion 175*b* can be separated by a neck portion (not shown), which can be the same as or generally similar to the neck portion 110*c* of the device 100 (FIG. 1C). However, the anchor structure 175 has a different shape than the anchor structure 110 (FIGS. 1A-1D) or the anchor structure 155 (FIG. 1D). For example, the first anchoring portion 175*a* includes one or more first loops 176*a*, and the second anchoring portion 175*b* includes one or more second loops 176*b*. In some embodiments in which there are multiple first loops 176*a* or multiple second loops 176*b*, the multiple first loops 176*a* can be arranged in a stacked configuration in which the multiple first loops 176*a* substantially overlap, and/or the multiple second loops 176*b* can be arranged in a stacked configuration in which the multiple second loops 176*b* substantially overlap. However, unlike the anchor structure 155 of the device 150 (FIG. 1D), the one or more first loops 176*a* have a different shape than the one or more second loops 176*b*. For example, in the illustrated embodiment, the one or more first loops 176*a* have a triangular shape and the one or more second loops 176*b*** have a circular shape, although other shapes are possible.

As one skilled in the art will appreciate, the closure devices 150 and 170 are provided merely as examples of additional anchor structure configurations. Accordingly, the description of the closure device 100, including the description of the operation and advantages of the closure device 100, equally applies to the closure devices 150 and 170, except where the context clearly indicates otherwise. Moreover, the closure devices are not limited to the shapes and configurations shown in FIGS. 1A-1E, and can instead have other suitable shapes and configurations within the scope of the present technology.

Figure 2:
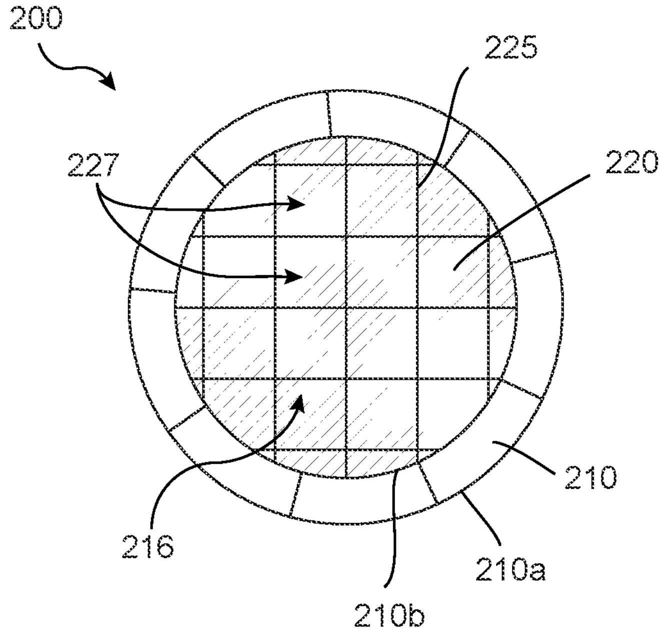
FIG. 2 illustrates another implantable closure device configured in accordance with select embodiments of the present technology.

The closure devices described herein can have additional features expected to improve one or more aspects of closure devices. FIG. 2, for example, is a front view of another closure device 200 ("the device 200") in a deployed configuration and configured in accordance with select embodiments of the present technology. The device 200 can include certain features generally similar to the device 100. For example, the device 200 can include an anchor structure 210 that is generally similar to or the same as the anchor structure 110 described above with reference to FIGS.

1A-1C. The anchor structure 210 can have an outer portion 210*a* (e.g., an outer circumference) and an inner portion 210*b* (e.g., an inner circumference) defining an aperture or empty space 216 extending therethrough. The device 200 can also include a membrane 220 coupled to the anchor structure 210 that covers or substantially covers the aperture 216 (portions of the membrane 220 are shown with surface shading lines for ease of illustration).

The device 200 differs from the device 100 described previously in that the device 200 further includes a plurality of structural members 225 that form a grid-like shape over the aperture 216. The structural members 225 can be embedded within the membrane 220, coupled to an outer surface of the membrane 220, simply positioned adjacent the membrane 220, or otherwise functionally coupled to the membrane 220. In some embodiments, for example, the membrane 220 is composed of two or more material layers laminated together, with the structural members 225 positioned between two of the layers. The structural members 225 can be relatively thin wire-like structures (e.g., having a diameter of less than about 2 mm, less than about 1 mm, etc.). The structural members 225 can also be at least partially pliable such that the shape of the grid can be changed by imparting a force on one or more individual structural members 225. In some embodiments, the structural members 225 can be suture wires, nitinol wires, silicone tubes, or other suitable materials that form a relatively thin and flexible filament.

Of note, the structural members 225 do not prevent a recrossing of the device 200. For example, during a recrossing, a percutaneous tool (e.g., a catheter with a puncture element) can be inserted through any one of a plurality of openings 227 defined by the grid-like shape of the structural members 225 to puncture the membrane 220 and any tissue overgrowth to provide access through the device 200. If the percutaneous tool contacts one of the structural members 225 during crossing, the percutaneous tool could be at least partially redirected into one of the openings 227. If the percutaneous tool is too large to fit through one of the openings 227, the structural member 225 would simply be deflected out of the way by virtue of its pliable configuration to increase the size of the opening 227 through which the percutaneous tool is inserted, enabling crossing of the percutaneous tool. In some embodiments, the structural members 225 are configured to rip or tear in a controlled fashion when stretched by a percutaneous tool. In some embodiments, the structural members 225 are not expected to provide substantial resistance during a recrossing procedure. In some embodiments, the grid size (e.g., the local density of filaments that define the openings 227) of the structural members 225 can vary across the membrane 220. This can enable different sections of the membrane 220 to have varying properties. Without being bound by theory, it is expected that a higher density of structural members 225 (e.g., creating smaller openings 227) will provide relatively more resistance to a tool during a recrossing, but following removal of the recrossing tool will enable the membrane 220 to more easily elastically recover to a configuration with a smaller residual opening.

The structural members 225 are expected to provide several advantages. For example, the structural members 225 are expected to function as a "tear stop" that reduces or prevents tearing (e.g., uncontrolled tearing) of patient tissue and/or the membrane 220 during a recrossing or other interaction (e.g., dilation, balloon expansion, etc.) by acting as reinforcement and/or stress distribution points. For example, in some embodiments the structural members 225 only permit tissue and/or the membrane 220 to open within the area defined by the opening 227 that a puncture is contained within. If larger access is needed, the structural members 225 can be dilated/expanded/stretched, but without incurring additional tearing of tissue and/or the membrane 220. When the dilation/expansion tool is removed, the size of the resulting hole in the tissue and/or membrane 220 will not be larger than the grid size created by the structural members 225.

The structural members 225 are also expected to augment the elastic recovery of the membrane 220 and/or tissue overgrowth of the membrane 220, and thereby limit the residual opening that remains in the membrane 220 and/or tissue following a puncture by the percutaneous tool during a recrossing. For example, the structural members 225 can have a preferred orientation (e.g., based upon their points of fixation to the anchor structure 210). In embodiments in which the structural members 225 are elastic or superelastic, following a deformation away from the preferred orientation (e.g., by a percutaneous tool during a recrossing), they will naturally return toward their preferred orientation following removal of the deformation force (e.g., upon withdrawal of the percutaneous tool). In some embodiments, this elastic recoil of the structural members 225 also moves the membrane 220 back toward an original position. In some embodiments, the membrane 220 also has elastic properties and the combined elasticity of the membrane 220 and the structural members 225 creates more complete reclosure of a puncture hole in the membrane 220. Of course, following elastic recovery of the structural members 225 and the membrane 220, a hole will still exist through one of the openings 227. However, in some embodiments the size of the hole through the corresponding opening 227 is relatively smaller than the hole size would be if the same percutaneous tool were advanced through a device without the structural members and/or directly through native patient tissue. Because the hole is smaller, it is expected that the hole will reclose/seal faster (e.g., via tissue overgrowth). Accordingly, the structural members 225 described herein are configured to automatically return to a state in which any opening or puncture is relatively small (e.g., having a dimension less than 5 mm, less than 3 mm, etc.) after a recrossing event, and thus are expected to be overgrown by tissue within a relatively short time (e.g., less than one week, less than one month, less than three months, etc.).

Figure 3:
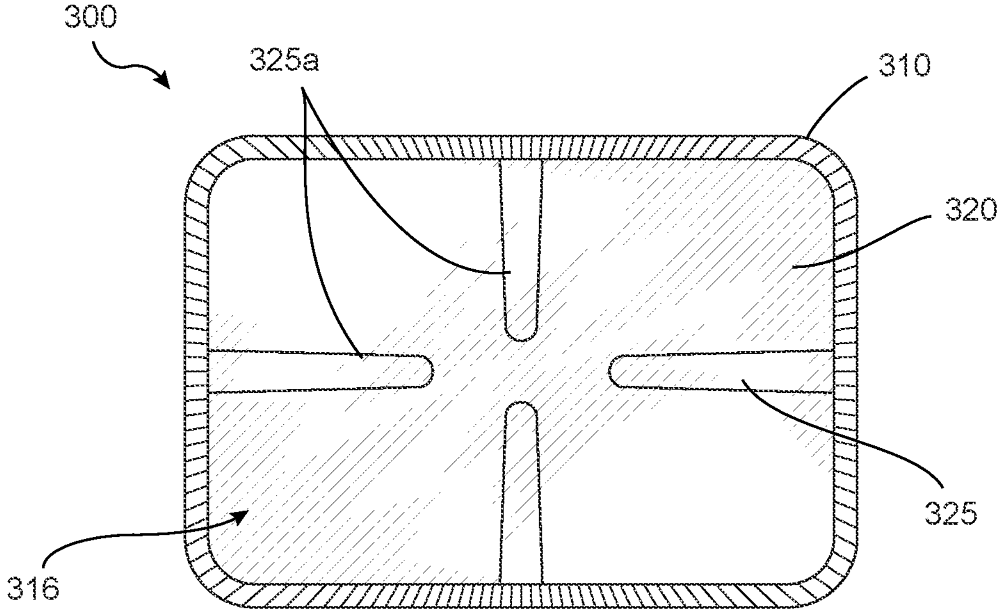
FIG. 3 illustrates another implantable closure device configured in accordance with select embodiments of the present technology.

The devices described herein can have structural members with other orientations beyond the grid-like shape shown in FIG. 2. FIG. 3, for example, illustrates yet another closure device 300 ("the device 300") in a deployed configuration and configured in accordance with select embodiments of the present technology. The device 300 can include certain features generally similar to the device 100 (FIGS. 1A-1C) and the device 200 (FIG. 2). For example, the device 300 can include an anchor structure 310 having a central aperture or empty space 316 extending therethrough, and a membrane 320 coupled to the anchor structure 310 that covers or substantially covers the aperture 316 (portions of the membrane 320 are shown with surface shading lines for ease of illustration). The device 300 also includes a plurality of structural members 325 extending inward from the anchor structure 310.

Relative to the structural members 225 described above with respect to FIG. 2, the structural members 325 of the device 300 have only a single attachment point to the anchor structure 310. The structural members 325 can therefore be referred to as "fingers." Each structural member 325 has a distal end portion 325*a* positioned radially inward from the anchor structure 310. In some embodiments, the distal end portions 325*a* are spaced apart from each other by a gap, although in other embodiments one or more of the distal end portions 325*a* may overlap. Although shown as having four structural members 325, the device 300 can have more or fewer structural members 325, such as one, two, three, five, six, seven, eight, or more.

In some embodiments, the structural members 325 can have a preferred orientation aligned with the plane of the membrane 320 (e.g., as shown in FIG. 3). After the device 300 has been deployed across an anatomical structure to close an opening or defect in the anatomical structure, the device 300 can be recrossed with another percutaneous tool. As the tool makes contact with the device 300 in the region of desired crossing, the structural members 325 guide the tool toward a central portion of the aperture 316 (e.g., as defined by the distal end portions 325*a* of the structural members 325). Depending on the size of the tool, the structural members 325 can then deflect out of the way (e.g., by being pushed into/normal to the plane in which they are illustrated) to permit the tool to puncture the membrane 220 and pass through the device 300. However, because the structural members 325 are coupled to the membrane, the structural members 325 are expected to reduce or prevent tearing of the membrane (or patient tissue grown over the membrane) in regions beyond the central portion of the aperture 316. Similar to the structural members 225 described above with reference to FIG. 2, the structural members 325 can be elastic, superelastic, or otherwise deformable and as such do not provide meaningful mechanical resistance to the tool during crossing, and can be held open easily by the presence of a catheter or tool that is positioned through the device 300. Once the tool is removed, the elasticity of the structural members 325 (along with the elasticity of the membrane 320) causes the structural members 325 to recoil toward their preferred orientation. As described above with respect to FIG. 2, this is expected to promote reclosing of the device 300 following the recrossing event by minimizing the size of the puncture made during the recrossing event.

Figure 4:
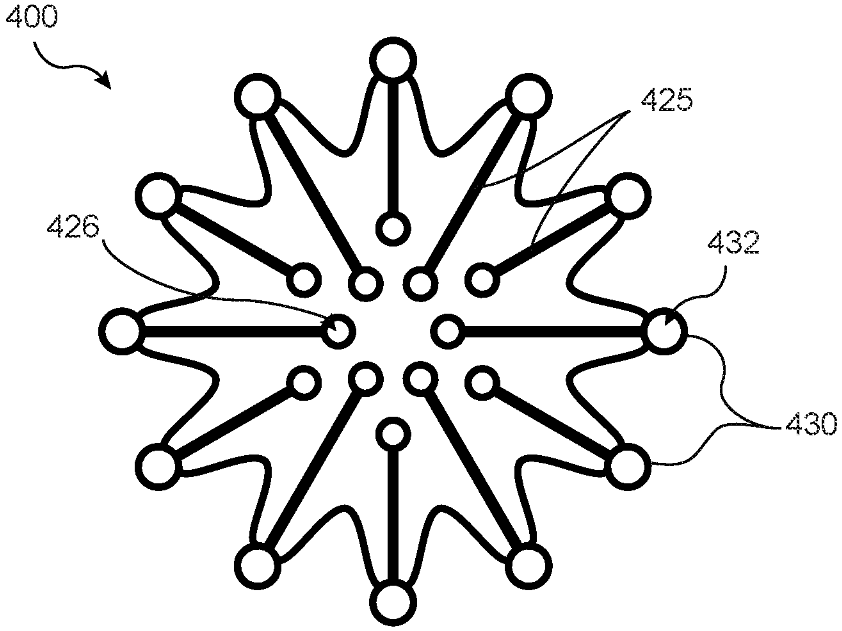
FIG. 4 illustrates an embedded structure for use with an implantable closure device and configured in accordance with select embodiments of the present technology.

FIG. 4 illustrates an embedded structure 400 having a plurality of structural members 425 and configured in accordance with select embodiments of the present technology. The embedded structure 400 can be used in combination with any of the closure devices described herein (e.g., the embedded structure 400 can be used with the device 200 shown in FIG. 2 in lieu of the structural members 225, or with the device 300 shown in FIG. 3 in lieu of the structural members 325). The embedded structure 400 includes a star-like shape having a plurality of vertices 430, each of which can have a corresponding vertex ring 432. The embedded structure 400 further includes structural members 425 projecting from each vertex 430 toward a central portion of the embedded structure 400. The distal end of each of the structural members 425 can include an inner ring 426. As described below, the inner ring 426 can be used to couple the embedded structure 400 to a membrane of a closure device (not shown). The inner rings 426 may optionally also hold one or more radio-opaque markers, in addition to or in lieu of being used to couple the embedded structure to a membrane.

The embedded structure 400 can be coupled to the anchor structure of a closure device, such as the anchor structure 110 of the device 100 (FIGS. 1A-1C), the anchor structure 210 of the device 200 (FIG. 2), or the anchor structure 310 of the device 300 (FIG. 3). For example, the embedded structure 400 can be sutured to an anchor structure by passing sutures through one or more of the vertex rings 432. The embedded structure 400 can also be coupled to a membrane of a closure device, such as the membrane 120 of the device 100 (FIGS. 1A-1C), the membrane 220 of the device 200 (FIG. 2), or the membrane 320 of the device 300 (FIG. 3). For example, the embedded structure 400 can be sutured to the membrane by passing sutures through one or more of the inner rings 426 on the structural members 425. As another example, the inner rings 426 can be filled with an adhesive (e.g., glue) to couple the embedded structure 400 to the membrane.

Once coupled to a closure device, the embedded structure 400 functions generally similar to the structural members described herein. For example, the structural members 425 of the embedded structure 400 can (1) reduce or prevent tearing of the membrane and/or patient tissue during a recrossing event, and (2) promote reclosure of the device through elastic recovery of the shape of the structural members 425 and by minimizing the size of the hole created through the corresponding closure device during a recrossing event. Although the embedded structure 400 is described herein as a component that is coupled to an anchoring structure of a closure device, the embedded structure 400 can also be coupled to a membrane and used by itself as a re-crossable closure device. In such embodiments, the embedded structure 400 can be directly coupled to patient tissue, e.g., by passing sutures through the vertex rings 432.

Figure 5A:
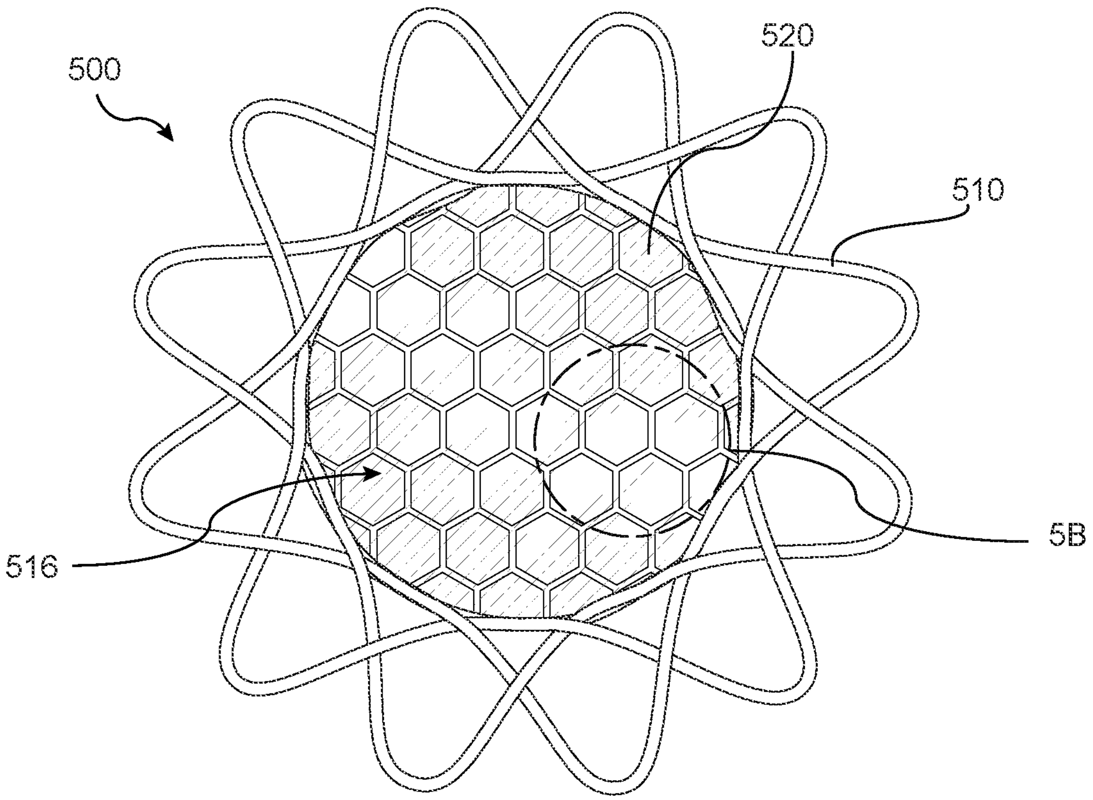
FIGS. 5A-5D illustrate another implantable closure device configured in accordance with select embodiments of the present technology.

Closure devices of the present technology can have other features, in addition to or in lieu of the structural members described with respect to FIGS. 2-4, that reduce uncontrolled tearing during a recrossing, reduce the magnitude of tearing during a recrossing, and/or minimize the size of any residual hole following a recrossing. FIG. 5A, for example, is a front view of another closure device 500 ("the device 500") in a deployed configuration and configured in accordance with select embodiments of the present technology. The device 500 can include certain features generally similar to the closure devices described above. For example, the device 500 can include an anchor structure 510 that is generally similar to or the same as the anchor structure 110 described above with reference to FIGS. 1A-1C. The anchor structure 510 can define an aperture or empty space 516 extending therethrough. The device 500 can also include a membrane 520 coupled to the anchor structure 510 that covers or substantially covers the aperture 516 (portions of the membrane 520 are shown with surface shading lines for purposes of illustration).

Figure 5B:
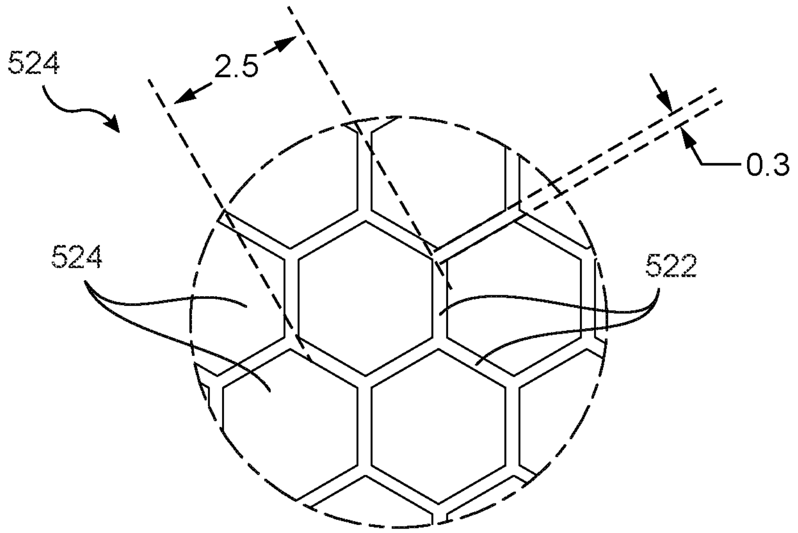

Rather than including structural members, however, the membrane 520 itself is configured to improve recrossing by, for example, reducing uncontrolled tearing during a recrossing, reducing the magnitude of tearing during a recrossing, and/or minimizing the size of any residual hole following a recrossing. In particular, the membrane 520 itself is formed by one or more materials such that the membrane 520 has a plurality of regions with different mechanical properties. For example, FIG. 5B is an enlarged view of a portion of the membrane 520 and illustrates a plurality of first regions 522 having a first set of mechanical properties and a plurality of second regions 524 having a second set of mechanical properties that differ from the first set of mechanical properties. For example, in some embodiments the first regions 522 have a first density and the second regions 524 have a second density less than the first density (in such embodiments the first regions 522 and the second regions 524 can therefore be referred to as high density regions and low density regions, respectively). In some embodiments, the first regions 522 have a first thickness and the second regions have a second thickness less than the first thickness (in such embodiments the first regions 522 and the second regions 524 can therefore be referred to as relatively thicker regions and relatively thinner regions, respectively). Of course, other structural differences can exist between the first regions 522 and the second regions 524 beyond variable densities and thicknesses.

In embodiments in which the first regions 522 have a greater thickness than the second regions 524, the first regions 522 can form a series of ridges that "extend" from the second regions 524. In such embodiments, the membrane 520 can be configured such that the ridges formed by the first regions 522 face a direction that a puncture tool will approach from during a recrossing event. For example, in embodiments in which the system 500 is deployed across a septal wall of a heart between a left atrium and a right atrium, the ridges formed by the first regions 522 can face (e.g., extend toward) the right atrium, since any puncture tool will generally approach the membrane 520 from the right atrium side. Without intending to be bound by theory, facing the ridges toward the side the puncture tool will approach from is expected to improve directing of the puncture tool into a second region 524 for puncturing the membrane 520, as described in greater detail below. However, in other embodiments, the ridges formed by the first region 522 can face (e.g., extend toward) the left atrium, and/or can simultaneously face both the right atrium and the left atrium (e.g., the second region 524 can extend from a mid-portion of the first regions 522).

The first regions 522 and the second regions 524 can form various patterns on the membrane 520. In the illustrated embodiments, for example, the second regions 524 have a hexagonal shape and the first regions 522 form a perimeter around the second regions 524, such that the first regions 522 and the second regions 524 form a honeycomb pattern. In other embodiments, the first regions 522 and/or the second regions 524 can have other suitable shapes/patterns, such as circular, oval-shape, triangular, rectangular, square, pentagonal, etc. In the illustrated embodiment, the pattern formed by the first regions 522 and the second regions 524 is regular or consistent across the membrane 520. In other embodiments, the pattern formed by the first regions 522 and the second regions 524 can be varied or irregular across the membrane 520. For example, the membrane 520 may have a first portion in which the first regions 522 are relatively more spaced apart such that the second regions 524 are relatively larger in size, and a second region in which the first regions 522 are relatively less spaced apart such that the second regions 524 are relative smaller in size. Regardless of the pattern, the first regions 522 and/or the second regions 524 can be formed of a semi-flexible and at least partially impermeable material. For example, the first regions 522 and/or the second regions 524 can be composed of silicone, polytetrafluoroethylene (PTFE), expanded polytetrafluoroethylene (ePTFE), polyethylene terephthalate (PET), a urethane (e.g., polyurethane/chronoflex), nylon, blends or composites thereof, or other similar material(s). In such embodiments, the first regions 522 and the second regions 524 can be formed via a mold having periodic ridges corresponding to the desired pattern of the membrane 520. In some embodiments, such as the embodiment described below with reference to FIG. 6, the honeycomb structure defined by the first regions 522 can be a separate element from, and composed of a different material than, the second regions 524.

The first regions 522 can function generally similar to the structural members described above. For example, during a recrossing, a percutaneous tool (e.g., a catheter with a puncture element) can be inserted through any one of the second regions 524 to puncture the membrane 520 and any tissue overgrowth to provide access through the device 500. If the percutaneous tool contacts one of the first regions 522 during crossing, the percutaneous tool could be at least partially redirected into one of the second regions 524, e.g., as a result of the different (e.g., stronger) mechanical properties at the first regions 522. If the percutaneous tool is too large to fit through one of the second regions 524, the first region 522 surrounding the second region 524 can be stretched (e.g., dilated, expanded, etc.) by virtue of its flexibility to accommodate the percutaneous tool. This can be performed by the percutaneous tool itself or a separate dilator.

Figure 5C:
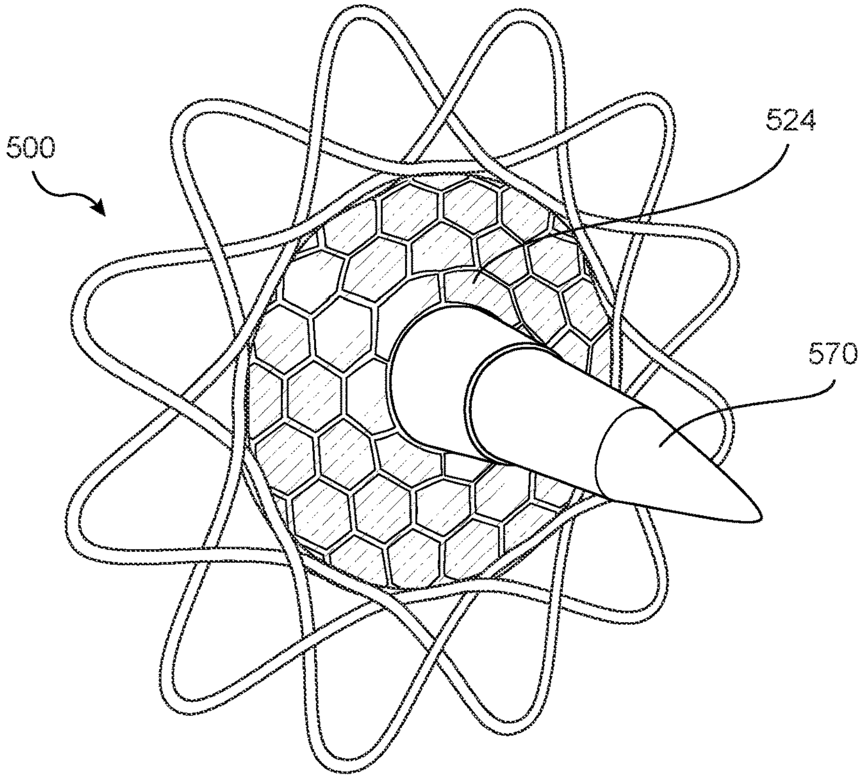

FIG. 5C illustrates an example of inserting a percutaneous tool 570 through a single second region 524 (not shown in FIG. 5A) by dilating the corresponding first region 522 surrounding the single second region 524. The percutaneous tool 570 has an outer diameter larger than the diameter of the corresponding second region 524. However, the first region 522 defining the corresponding second region 524 can be dilated to accommodate the percutaneous tool 570 such that the percutaneous tool 570 only punctures a single second region 524. Of note, the first region 522 does not tear as it is dilated, e.g., as result of its (e.g., stronger) mechanical properties. Accordingly, the first regions 522 can function as a "tear stop" that reduces or prevents tearing (e.g., uncontrolled tearing) of patient tissue and/or the membrane 520 during a recrossing or other interaction (e.g., dilation, balloon expansion, etc.) by acting as reinforcement and/or stress distribution points.

Figure 5D:
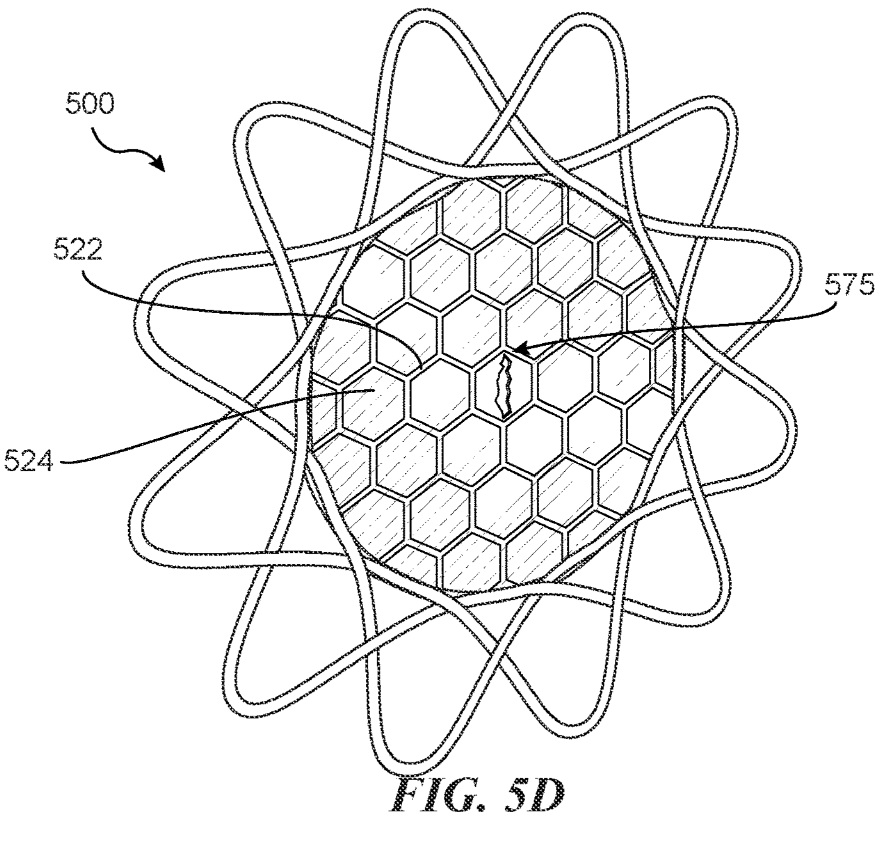

The first regions 522 can also be elastic or otherwise biased toward their original deployed configuration (e.g., a pre-recrossing configuration), such as the configuration shown in FIG. 5A. As a result, following removal of the percutaneous tool and as shown in FIG. 5D, the first region 522 returns toward its original, pre-dilated configuration. Because only a single second region 524 was punctured during the recrossing, only a relatively small residual hole 575 remains in the membrane 520. Without being bound by theory, the size of the residual hole 575 through the membrane 520 is relatively smaller than the hole size would be if the same percutaneous tool were advanced through a device without the first regions 522 and/or directly through native patient tissue. Indeed, in some embodiments the size (e.g., length) of the residual hole 575 is expected to be less than the size (e.g., diameter) of the percutaneous tool 570 that was advanced through the membrane 520. Because the hole 575 is smaller, it is expected that the hole will reclose/seal faster (e.g., via tissue overgrowth). Accordingly, the first regions 522 are configured to automatically return to a state in which any opening or puncture is relatively small (e.g., having a dimension less than 5 mm, less than 3 mm, etc.) after a recrossing event, and thus are expected to be overgrown by tissue within a relatively short time (e.g., less than one week, less than one month, less than three months, etc.).

Figure 6:
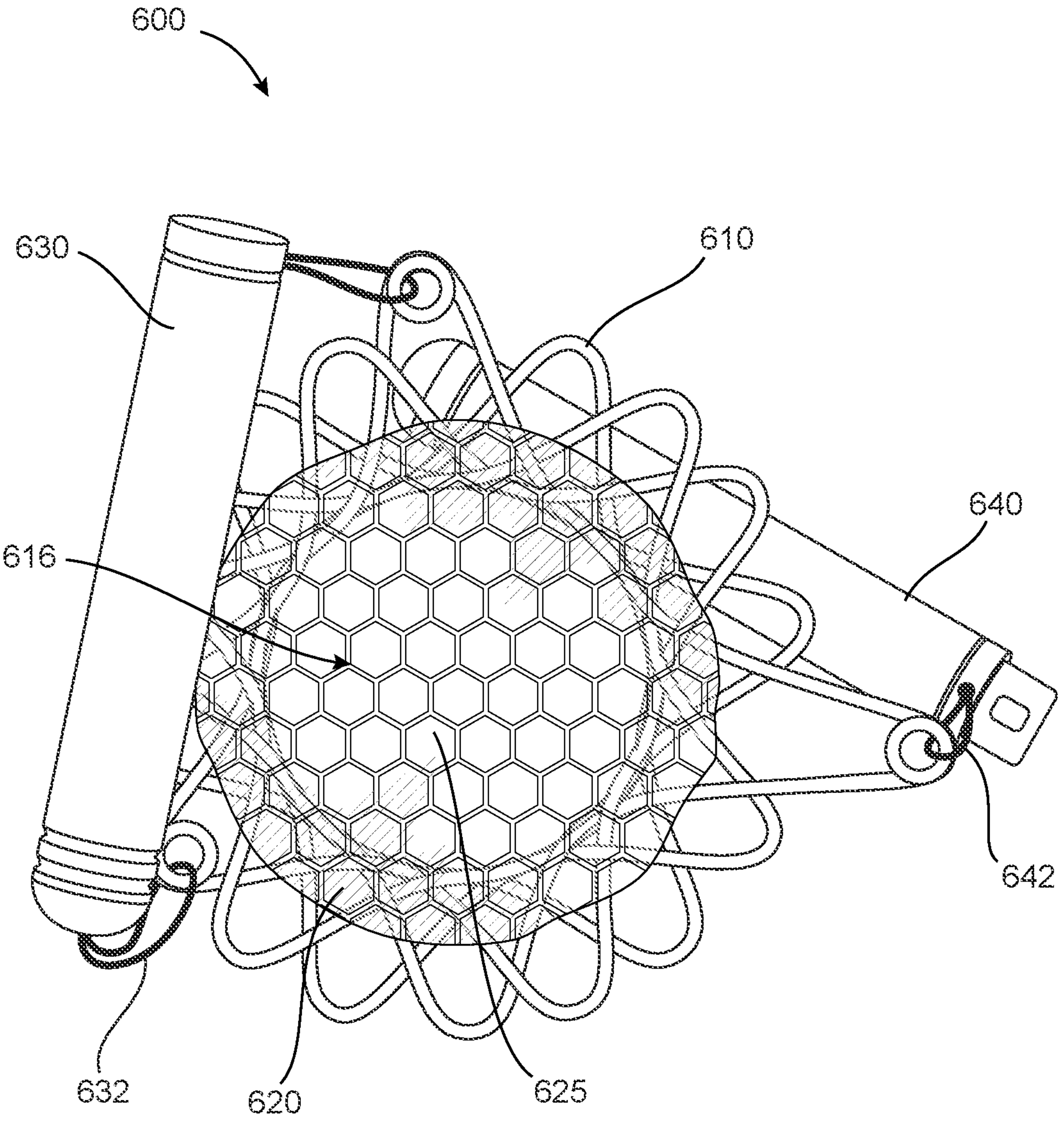
FIG. 6 illustrates another implantable closure device having storage canisters and configured in accordance with select embodiments of the present technology.

FIG. 6 is a front view of another closure device 600 ("the device 600") in a deployed configuration and configured in accordance with select embodiments of the present technology. The device 600 can include certain features generally similar to the closure devices described above. For example, the device 600 can include an anchor structure 610 generally similar to or the same as the anchor structure 110 described above with reference to FIGS. 1A-1C, and/or the anchor structure 510 described above with reference to FIGS. 5A-5D. The anchor structure 610 can define an aperture or empty space 616 extending therethrough. The device 600 also includes a membrane 620 coupled to the anchor structure 610 that covers or substantially covers the aperture 616 to occlude flow of fluid therethrough (portions of the membrane 620 are shown with surface shading lines for ease of illustration).

Similar to the device 500 described with reference to FIGS. 5A-5D, the device 600 includes a honeycomb shaped or other porous structure 625. However, unlike the device 500 in which the honeycomb shape is created by virtue of varying the thickness, density, and/or other structural characteristic of the membrane 520 itself, the honeycomb structure 625 is a separate component from the membrane 620. Accordingly, the honeycomb structure 625 can have a plurality of circular, square, pentagonal, hexagonal, or other shaped openings extending therethrough. To provide occlusion (e.g., to prevent fluid from flowing through the openings in the honeycomb structure 625), the honeycomb structure 625 can be coupled to the membrane 620. For example, in some embodiments the membrane 620 includes two or more layers that can be laminated together, with the honeycomb structure 625 positioned therebetween. In some embodiments, the membrane 620 is glued or otherwise connected to the portions of the honeycomb structure 625 that define the openings, which enables the membrane to stretch and contract in concert with individual openings in the honeycomb structure 625 during a recrossing event, as described in detail below. Without being bound by theory, providing a separate honeycomb structure 625 and membrane 620 may be easier and/or cheaper to manufacture than a single structure with the varying structural properties of the device 500 of FIGS. 5A-5D. Similarly, providing a separate honeycomb structure 625 and membrane 620 may enable these features to be composed of different materials that are selected based at least in part on their corresponding functions. For example, the honeycomb structure 625 can be composed of a biocompatible polymer that minimizes ripping of the honeycomb structure 625, while the membrane 620 can be composed of a material that encourages tissue overgrowth to promote reclosure of any hole through the device 600.

In operation, the device 600 functions similarly to the device 500 described with reference to FIGS. 5A-5D. For example, during a recrossing event, a percutaneous tool can puncture the membrane 620 and pass through a single opening in the honeycomb structure 625. Depending on the size of the percutaneous tool, the opening in the honeycomb structure 625 can dilate or otherwise expand as the percutaneous tool is advanced through it. In embodiments in which the membrane 620 is glued or otherwise coupled to the honeycomb structure 625, the membrane 620 also stretches/deforms in concert with the opening in the honeycomb structure 625. Upon removal of the percutaneous tool, both the opening in the honeycomb structure 625 and the membrane 620 can return to their pre-dilated or pre-expanded size and shape. Thus, similar to the embodiments described above, the device 600 can reduce uncontrolled tearing of the membrane 620 and/or minimize the size of any residual hole through the device 600 following a recrossing event. If the tool being passed through the opening is large enough, it may rupture the opening in the honeycomb structure 625. However, even in such embodiments, the adjacent cells of the honeycomb structure 625 will limit the tearing/ripping to the single opening, minimizing the size of any residual hole through the device 600 following a recrossing event.

The device 600 can also include a first housing or canister 630 coupled to a first (e.g., left atrial) side of the anchor structure 610, and a second housing or canister 640 coupled to a second (e.g., right atrial) side of the anchor structure 610. More specifically, the first canister 630 can be coupled to the anchor structure 610 via one or more first mechanical connectors 632, and the second canister 640 can be coupled to the anchor structure 610 via one or more second mechanical connectors 642. Additional details regarding connecting canisters to anchor structures such as the anchor structure 610 are described in International Patent Application No. PCT/US2022/046584, the disclosure of which is incorporated by reference herein in its entirety.

The canisters 630, 640 can be hermetically sealed containers that house various electronics or other components of or associated with the device 600. For example, the canisters 630, 640 can house one or more energy storage components (e.g., a battery, a capacitor, a supercapacitor, etc.), one or more sensors (e.g., a pressure sensor, a flow sensor, etc.), electronic circuitry associated with one or more sensors, one or more data storage elements (e.g., memory), one or more processors, one or more telemetry components, one or more radios, one or more microcontrollers, or the like. Additional details regarding canisters and associated components that can be used in combination with the device 600 are described in U.S. Patent Application Publication No. US2021/0370032, the disclosure of which is incorporated by reference herein in its entirety. Moreover, although shown as having the first canister 630 on the first side of the device 600 and the second canister 640 on the second side of the device 600, in other embodiments the device 600 can include more or fewer canisters (e.g., zero, two, three, etc.) on either side. Similarly, the device 600 can include more or fewer than two total canisters, such as one, three, four, five, six, or more canisters.

As described above, one expected advantage of some embodiments of the present technology is the ability to have a re-crossable closure device that (1) reduces uncontrolled tearing and/or the magnitude of tearing of patient tissue and/or a membrane of the closure device, and (2) minimizes the size of any puncture hole created in the membrane and/or patient tissue that has grown over the membrane. In some embodiments, this is accomplished by utilizing one or more structural members coupled to the membrane, membrane regions of varying densities or thicknesses, or the like. Moreover, although the structural members are described as being elastic or superelastic such that, following a re-crossing procedure, they automatically recoil toward their preferred orientation, in other embodiments the structural members are not elastic and do not automatically return to their preferred orientation following removal of the force that caused the deformation. For example, in some embodiments, the structural members described herein can be manufactured to have shape memory properties such that they are in a martensitic or other deformable material state at body temperature. In such embodiments, crossing the device with a catheter would deflect the structural members out of the way mechanically, and the structural members would remain in this deformed/deflected position rather than automatically recoil toward their preferred configuration. This would provide a large amount of clearance through the device and have the advantage of not having the structural members provide any friction or resistance to the tool while it is across the device or during removal of the tool. To move the structural members back into the original orientation (e.g., in order to facilitate closure or near-closure of the puncture hole), the structural members can be heated above a material transition temperature (e.g., to transition from the martensitic material state to an austenitic material state). The structural members could be heated through any suitable mechanism, such as those described in International Patent Application Nos. PCT/US21/53836, filed Oct. 6, 2021, PCT/US21/55191, filed Oct. 15, 2021, and PCT/US21/58996, filed Nov. 11, 2021, each of which is incorporated by reference herein in its entirety.

Moreover, although the closure devices described herein are configured to have a flat or substantially flat profile relative to the plane of the anatomical structure across which they are deployed (e.g., the septal wall), in other embodiments the devices may include one or more components that protrude into a body region (e.g., the right atrium) adjacent the anatomical structure. The components that protrude into the body region can be configured to open and close to permit a re-crossing of the device. For example, the component could be mechanically expandable via a balloon and thermally contractable via a shape memory effect, similar to the adjustable shunts described in International Patent Application No. PCT/US21/58996, the disclosure of which was previously incorporated by reference herein. However, relative to the adjustable shunts described in International Patent Application No. PCT/US21/58996, the closure devices are configured such that, when thermally contracted, the closure device assumes either a fully closed position (e.g., preventing flow or access through the device) or substantially closed position with a relatively small opening (e.g., of less than 3 mm in diameter) that would be expected to be overgrown by tissue relatively quickly. To re-cross the device, a guidewire could be advanced through the device, and a balloon could be inflated to mechanically expand the closure device to provide access for another percutaneous tool.

The closure devices described herein can also promote other functions and/or be integrated with other implantable components. For example, in some embodiments, the anchor structures (e.g., the anchor structure 110 of the device 100, the anchor structure 155 of the device 150, the anchor structure 175 of the device 170, the anchor structure 210 of the device 200, the anchor structure 310 of the device 300, and/or the anchor structure 510 of the device 500) can further be configured to receive and/or generate energy/power when communicatively coupled to an energy source, in addition to stabilizing the device across the anatomical structure. For example, in some embodiments, the wire(s) or filament(s) utilized to form the anchor structure constitute one or more inductive portions of a circuit configured to generate energy when exposed to an electromagnetic field. The energy generated by the anchor structure can be stored and/or used to power various active components implanted with the device (e.g., a sensor, which can be housed in or carried by the canisters 630, 640 of the device 600 shown in FIG. 6). To facilitate inductive charging using the anchor structure, some or all of the anchor structure can include a relatively conductive material (e.g., silver). For example, the wire(s) or filament(s) that are used to construct the anchor structure can be highly conductive themselves (e.g., silver), have a highly conductive core surrounded by a less conductive (e.g., nitinol) sheath or coating, a less conductive core with a highly conductive sheath or coating, a highly conductive wire coupled to a less conductive wire, or another suitable arrangement. In such embodiments involving a composite structure, the less conductive portion generally provides the majority of the structural performance (e.g., anchoring) whereas the more conductive portion generally provides the majority of the electrical performance (e.g., energy/power transfer).

As one of skill in the art will appreciate from the disclosure herein, various components of the systems described above can be omitted without deviating from the scope of the present technology. Likewise, additional components not explicitly described above may be added to the systems without deviating from the scope of the present technology. Moreover, the features described herein can be incorporated into other types of implantable medical devices beyond closure devices. Accordingly, the present technology is not limited to the configurations expressly identified herein, but rather encompasses variations and alterations of the described systems.

Examples

Several aspects of the present technology are set forth in the following examples:

1. A recrossable closure device for treating a patient, the closure device comprising:
   an anchor structure configured to extend through an opening in an anatomical structure separating a first body region and a second body region of the patient, wherein the anchor structure is configured to anchor the device to the anatomical structure, and has an aperture spanning at least a portion thereof; and
   a membrane coupled to the anchor structure and covering the aperture, wherein, when the device is implanted in the opening, the membrane is configured to fluidly separate the first body region and the second body region,
   wherein, after implantation, the device is configured to enable a recrossing of a surgical tool between the first body region and the second body region via puncturing of the membrane to provide access therebetween, and wherein the device is further configured to limit tearing of patient tissue during the recrossing.
2. The recrossable closure device of example 1 wherein the anchor structure has a neck portion configured to extend through the opening in the anatomical structure, and wherein the neck portion is transitionable between a low-profile delivery configuration and a deployed configuration.
3. The recrossable closure device of example 2 wherein the neck portion is configured to change a shape of the opening when positioned within the opening and transitioned between the low-profile delivery configuration and the deployed configuration.
4. The recrossable closure device of example 2 or example 3 wherein the neck portion is configured to increase a dimension of the opening when positioned within the opening and transitioned between the low-profile delivery configuration and the deployed configuration.
5. A closure device for treating a patient, the closure device comprising:
   an anchor structure configured to extend through an opening in an anatomical structure separating a first body region and a second body region, wherein the anchor structure is configured to anchor the device to the anatomical structure, and has an aperture spanning at least a portion thereof;
   a membrane coupled to the anchor structure and covering the aperture, wherein, when the device is implanted in the opening, the membrane is configured to fluidly separate the first body region and the second body region; and one or more structural members extending at least partially across the aperture, wherein the one or more structural members are embedded within or otherwise coupled to the membrane, and wherein the one or more structural members are at least partially deformable.

6. The closure device of example 5 wherein the anchor structure has a neck portion configured to extend through the opening in the anatomical structure, and wherein the neck portion is transitionable between a low-profile delivery configuration and a deployed configuration.

7 The closure device of example 6 wherein the neck portion is configured to change a shape of the opening when positioned within the opening and transitioned between the low-profile delivery configuration to the deployed configuration.

8. The closure device of example 6 or example 7 wherein the neck portion is configured to increase a dimension of the opening when positioned within the opening and transitioned between the low-profile delivery configuration to the deployed configuration.

9. The closure device of any of examples 5-8 wherein the one or more structural members are configured to deform relative to a preferred orientation when contacted by a percutaneous tool to facilitate crossing of the percutaneous tool through the closure device.

10. The closure device of example 9 wherein, when in the preferred orientation, the one or more structural members are parallel to a plane defined by the membrane, and wherein the one or more structural members are configured to remain within the plane defined by the membrane when deformed.

11. The closure device of example 9 wherein, when in the preferred orientation, the one or more structural members are parallel to a plane defined by the membrane, and wherein the one or more structural members are configured to deflect in a direction normal to the plane defined by the membrane when deformed.

12. The closure device of any of examples 9-11 wherein the one or more structural members are elastic or superelastic such that the one or more structural members are configured to automatically return toward the preferred orientation following removal of the percutaneous tool.

13. The closure device of any of examples 5-12 wherein the one or more structural members are coupled to the anchor structure.

14. The closure device of any of examples 5-13 wherein the one or more structural members form a grid-like shape over the aperture.

15. The closure device of any of examples 5-14 wherein the one or more structural members extend radially inward from the anchor structure toward a central portion of the aperture, and wherein each of the one or more structural members includes a free end unconnected to the anchor structure.

16. The closure device of any of examples 5-15 wherein the one or more structural members are configured to reduce tearing of the membrane and/or reduce tearing of patient tissue overgrown over the membrane.

17. The closure device of any of examples 5-16 wherein the one or more structural members include a honeycomb structure having a plurality of openings extending therethrough.

18. The closure device of any of examples 5-17 wherein the membrane has a textured surface.

19. The closure device of any of examples 5-18 wherein the membrane has a durometer of between about 75A and 90A.

20. A closure device for treating a patient, the closure device comprising:

an anchor structure configured to extend through an opening in an anatomical structure separating a first body region and a second body region, wherein the anchor structure is configured to anchor the device to the anatomical structure, and has an aperture spanning at least a portion thereof;

a membrane carried by the anchor structure and covering the aperture, wherein, when the device is implanted in the opening, the membrane is configured to fluidly separate the first body region and the second body region, and wherein the membrane includes— one or more first regions having a first set of mechanical properties, and one or more second regions having a second set of mechanical properties different than the first set of mechanical properties, wherein, after implantation, the device is configured to enable a recrossing of a surgical tool between the first body region and the second body region via puncturing of an individual second region of the one or more second regions of the membrane, and wherein the one or more first regions of the membrane are configured to contain tearing of the membrane to the individual second region.

21. The closure device of example 20 wherein the one or more first regions are configured to dilate without tearing to accommodate the surgical tool during the recrossing.

22. The closure device of example 21 wherein the one or more first regions are biased toward a pre-dilated configuration.

23. The closure device of any of examples 20-22 wherein the one or more first regions and the one or more second regions are formed by a contiguous piece of material.

24. The closure device of any of examples 20-22 wherein the membrane includes a porous structure forming the one or more first regions and a laminate portion covering the porous structure, and wherein material forming the porous structure corresponds to the one or more first regions and openings in the porous structure correspond to the one or more second regions.

25. The closure device of any of examples 20-24 wherein the one or more first regions have a first thickness and the one or more second regions have a second thickness, and wherein the first thickness is greater than the second thickness.

26. The closure device of any of examples 20-25 wherein the device is configured such that, after a recrossing of the surgical tool, a residual hole in the membrane has a length that is smaller than a diameter of the surgical tool.

27. A method of closing an opening in an anatomical structure, the method comprising:

implanting a closure device within the opening such that an expandable neck portion of the closure device passes through the opening; and expanding the expandable neck portion of the closure device to a deployed configuration, wherein expanding the neck portion of the closure device to the deployed configuration (1) reshapes the opening and (2) increases at least one dimension associated with the opening, wherein the closure device includes a membrane that at least partially seals the opening when the closure device is in the deployed configuration.

28. The method of example 27 wherein implanting the closure device includes advancing the closure device from a catheter, and wherein expanding the expandable neck portion includes automatically expanding the neck portion upon deployment of the closure device from the catheter.

29. The method of example 27 or example 28 wherein the at least one dimension is a surface area of the opening.

30. The method of example 27 or example 28 wherein the at least one dimension is a diameter of the opening.

CONCLUSION

Embodiments of the present disclosure may include some or all of the following components: a battery, supercapacitor, or other suitable power source; a microcontroller, FPGA, ASIC, or other programmable component or system capable of storing and executing software and/or firmware that drives operation of an implant; memory such as RAM or ROM to store data and/or software/firmware associated with an implant and/or its operation; wireless communication hardware such as an antenna system configured to transmit via Bluetooth, WiFi, or other protocols known in the art; energy harvesting means, for example a coil or antenna which is capable of receiving and/or reading an externally-provided signal which may be used to power the device, charge a battery, initiate a reading from a sensor, or for other purposes. Embodiments may also include one or more sensors, such as pressure sensors, impedance sensors, accelerometers, force/strain sensors, temperature sensors, flow sensors, optical sensors, cameras, microphones or other acoustic sensors, ultrasonic sensors, ECG or other cardiac rhythm sensors, SpO2 and other sensors adapted to measure tissue and/or blood gas levels, blood volume sensors, and other sensors known to those who are skilled in the art. Embodiments may include portions that are radiopaque and/or ultrasonically reflective to facilitate image-guided implantation or image guided procedures using techniques such as fluoroscopy, ultrasonography, or other imaging methods. Embodiments of the system may include specialized delivery catheters/systems that are adapted to deliver an implant and/or carry out a procedure. Systems may include components such as guidewires, sheaths, dilators, and multiple delivery catheters. Components may be exchanged via over-the-wire, rapid exchange, combination, or other approaches.

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments. For example, although this disclosure has been written to describe devices that are generally described as being used to close a path of fluid communication between the left atrium and the right atrium, it should be appreciated that similar embodiments could be utilized for closure devices between other chambers of the heart or for closure devices in other regions of the body.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A recrossable closure device for treating a patient, the closure device comprising:

an anchor structure configured to extend through an opening in an anatomical structure separating a first body region and a second body region of the patient, wherein the anchor structure is configured to anchor the device to the anatomical structure, and has an aperture spanning at least a portion thereof; and a membrane coupled to the anchor structure and covering the aperture, wherein the membrane includes one or more members dividing the membrane into a plurality of penetration zones, and wherein, when the device is implanted in the opening, the membrane is configured to fluidly separate the first body region and the second body region, wherein, after implantation, the device is configured to enable a recrossing of a surgical tool between the first body region and the second body region via puncturing and tearing of an individual penetration zone of the plurality of penetration zones to provide access therebetween, and wherein the one or more members are configured to limit tearing of the membrane to the individual penetration zone during the recrossing.

2. The recrossable closure device of claim 1 wherein the anchor structure has a neck portion configured to extend through the opening in the anatomical structure, and wherein the neck portion is transitionable between a low-profile delivery configuration and a deployed configuration.

3. The recrossable closure device of claim 2 wherein the neck portion is configured to change a shape of the opening when positioned within the opening and transitioned between the low-profile delivery configuration and the deployed configuration.

4. The recrossable closure device of claim 2 wherein the neck portion is configured to increase a dimension of the opening when positioned within the opening and transitioned between the low-profile delivery configuration and the deployed configuration.

5. A closure device for treating a patient, the closure device comprising:

an anchor structure configured to extend through an opening in an anatomical structure separating a first body region and a second body region, wherein the anchor structure is configured to anchor the device to the anatomical structure, and has an aperture spanning at least a portion thereof;

a membrane coupled to the anchor structure and covering the aperture, wherein, when the device is implanted in the opening, the membrane is configured to fluidly separate the first body region and the second body region; and one or more structural members extending at least partially across the aperture, wherein the one or more structural members are embedded within or otherwise coupled to the membrane and divide the membrane into a plurality of regions, and wherein the one or more structural members are at least partially deformable, wherein, when a surgical tool pierces and tears an individual region of the plurality of regions of the membrane, the one or more structural members are configured to contain tearing of the membrane to the individual region.

6. The closure device of claim 5 wherein the anchor structure has a neck portion configured to extend through the opening in the anatomical structure, and wherein the neck portion is transitionable between a low-profile delivery configuration and a deployed configuration.

7. The closure device of claim 6 wherein the neck portion is configured to change a shape of the opening when positioned within the opening and transitioned between the low-profile delivery configuration to the deployed configuration.

8. The closure device of claim 6 wherein the neck portion is configured to increase a dimension of the opening when positioned within the opening and transitioned between the low-profile delivery configuration to the deployed configuration.

9. The closure device of claim 5 wherein the one or more structural members are configured to deform relative to a preferred orientation when contacted by a percutaneous tool to facilitate crossing of the percutaneous tool through the closure device.

10. The closure device of claim 9 wherein, when in the preferred orientation, the one or more structural members are parallel to a plane defined by the membrane, and wherein the one or more structural members are configured to remain within the plane defined by the membrane when deformed.

11. The closure device of claim 9 wherein, when in the preferred orientation, the one or more structural members are parallel to a plane defined by the membrane, and wherein the one or more structural members are configured to deflect in a direction normal to the plane defined by the membrane when deformed.

12. The closure device of claim 9 wherein the one or more structural members are elastic or superelastic such that the one or more structural members are configured to automatically return toward the preferred orientation following removal of the percutaneous tool.

13. The closure device of claim 5 wherein the one or more structural members are coupled to the anchor structure.

14. The closure device of claim 5 wherein the one or more structural members form a grid-like shape over the aperture.

15. The closure device of claim 5 wherein the one or more structural members extend radially inward from the anchor structure toward a central portion of the aperture, and wherein each of the one or more structural members includes a free end unconnected to the anchor structure.

16. The closure device of claim 5 wherein the one or more structural members are configured to reduce tearing of the membrane and/or reduce tearing of patient tissue overgrown over the membrane.

17. The closure device of claim 5 wherein the one or more structural members include a honeycomb structure having a plurality of openings extending therethrough.

18. The closure device of claim 5 wherein the membrane has a textured surface.

19. The closure device of claim 5 wherein the membrane has a durometer of between about 75A and 90A.

20. A closure device for treating a patient, the closure device comprising:

an anchor structure configured to extend through an opening in an anatomical structure separating a first body region and a second body region, wherein the anchor structure is configured to anchor the device to the anatomical structure, and has an aperture spanning at least a portion thereof;

a membrane carried by the anchor structure and covering the aperture, wherein, when the device is implanted in the opening, the membrane is configured to fluidly separate the first body region and the second body region, and wherein the membrane includes one or more first regions dividing the membrane into a plurality of second regions, wherein— the one or more first regions have a first set of mechanical properties, and the plurality of second regions have a second set of mechanical properties different than the first set of mechanical properties, wherein, after implantation, the device is configured to enable a recrossing of a surgical tool between the first body region and the second body region via puncturing and tearing of an individual second region of the plurality of second regions of the membrane, and wherein the one or more first regions of the membrane are configured to contain tearing of the membrane to the individual second region.

21. The closure device of claim 20 wherein the one or more first regions are configured to dilate without tearing to accommodate the surgical tool during the recrossing.

22. The closure device of claim 21 wherein the one or more first regions are biased toward a pre-dilated configuration.

23. The closure device of claim 20 wherein the one or more first regions and the one or more second regions are formed by a contiguous piece of material.

24. The closure device of claim 20 wherein the membrane includes a porous structure forming the one or more first regions and a laminate portion covering the porous structure, and wherein material forming the porous structure corresponds to the one or more first regions and openings in the porous structure correspond to the one or more second regions.

25. The closure device of claim 20 wherein the one or more first regions have a first thickness and the one or more second regions have a second thickness, and wherein the first thickness is greater than the second thickness.

26. The closure device of claim 20 wherein the device is configured such that, after a recrossing of the surgical tool, a residual hole in the membrane has a length that is smaller than a diameter of the surgical tool.

27. A method of closing an opening in an anatomical structure, the method comprising:

implanting a closure device within the opening such that an expandable neck portion of the closure device passes through the opening;

expanding the expandable neck portion of the closure device to a deployed configuration, wherein expanding the neck portion of the closure device to the deployed configuration (1) reshapes the opening and (2) increases at least one dimension associated with the opening, wherein the closure device includes a membrane that at least partially seals the opening when the closure device is in the deployed configuration, and wherein the membrane includes a first region dividing the membrane into a plurality of second regions; and advancing a surgical tool through the closure device by puncturing and tearing an individual second region of the plurality of second regions of the membrane, wherein the first region of the membrane contains tearing of the membrane to the individual second region.

28. The method of claim 27 wherein implanting the closure device includes advancing the closure device from a catheter, and wherein expanding the expandable neck portion includes automatically expanding the neck portion upon deployment of the closure device from the catheter.

29. The method of claim 27 wherein the at least one dimension is a surface area of the opening.

30. The method of claim 27 wherein the at least one dimension is a diameter of the opening.

* * * * *